(12) United States Patent
Askovich et al.

(10) Patent No.: US 12,362,040 B2
(45) Date of Patent: Jul. 15, 2025

(54) SYSTEMS AND METHODS FOR SPATIAL MAPPING OF EXPRESSION PROFILING

(71) Applicant: Bruker Spatial Biology, Inc., Seattle, WA (US)

(72) Inventors: Peter Askovich, Seattle, WA (US); Gayathri Balasundaram, Sammamish, WA (US); Joseph M. Beechem, Eugene, OR (US); Michael McKean, Gig Harbor, WA (US); Bishop Wilkins, Seattle, WA (US)

(73) Assignee: Bruker Spatial Biology, Inc., Seattle, WA (US)

( * ) Notice: Subject to any disclaimer, the term of this patent is extended or adjusted under 35 U.S.C. 154(b) by 0 days.

(21) Appl. No.: 17/768,625

(22) PCT Filed: Oct. 16, 2020

(86) PCT No.: PCT/US2020/056035
§ 371 (c)(1),
(2) Date: Apr. 13, 2022

(87) PCT Pub. No.: WO2021/076928
PCT Pub. Date: Apr. 22, 2021

(65) Prior Publication Data
US 2024/0296549 A1   Sep. 5, 2024

Related U.S. Application Data

(60) Provisional application No. 62/916,990, filed on Oct. 18, 2019.

(51) Int. Cl.
*G16B 25/00* (2019.01)
*G06T 7/00* (2017.01)
(Continued)

(52) U.S. Cl.
CPC ............ *G16B 25/00* (2019.02); *G06T 7/0012* (2013.01); *G06T 9/00* (2013.01); *G06V 10/25* (2022.01);
(Continued)

(58) Field of Classification Search
CPC ...... G16B 25/00; G06V 10/25; G06V 20/695; G06T 7/0012; G06T 9/00
See application file for complete search history.

(56) References Cited

U.S. PATENT DOCUMENTS

| 5,650,844 A | 7/1997 | Aoki et al. |
| 6,788,359 B2 | 9/2004 | Lee et al. |

(Continued)

FOREIGN PATENT DOCUMENTS

| CN | 1357753 A | 7/2002 |
| CN | 201166604 Y | 12/2008 |

(Continued)

OTHER PUBLICATIONS

Blank, et al., Neoadjuvant versus adjuvant ipilimumab plus nivolumab in macroscopic stage III melanoma, Nature medicine, Nov. 2018, pp. 1655-1661, vol. 24, No. 11.

(Continued)

*Primary Examiner* — David Bilodeau
(74) *Attorney, Agent, or Firm* — Shay Glenn LLP

(57) ABSTRACT

Systems, apparatuses and methods for spatially mapping at least one biological expression of a target biological component contained in a tissue sample to an image of the tissue sample are provided. In some embodiments, the system includes a processor and instructions that, when executed by the processor, cause the system to display, in a first display, a scans pane including at least the image of the tissue sample, the image including at least one demarcation corresponding to a region-of-interest (ROI(s)), where the ROI
(Continued)

(s) correspond to a portion of the tissue within the tissue image. The instructions are further configured to cause the system to display, in a second display, a visualization pane including a visualization of the biological expression contained in the ROI(s); and to augment the first display by coding the ROI(s) in the tissue image to show the spatial mapping of the biological expression within the ROI(s).

19 Claims, 26 Drawing Sheets

(51) Int. Cl.
   *G06T 9/00* (2006.01)
   *G06V 10/25* (2022.01)
   *G06V 20/69* (2022.01)

(52) U.S. Cl.
   CPC .. *G06V 20/695* (2022.01); *G06T 2207/20036* (2013.01); *G06T 2207/30024* (2013.01)

(56) References Cited

U.S. PATENT DOCUMENTS

| | | | |
|---|---|---|---|
| 6,972,892 | B2 | 12/2005 | Desimone et al. |
| 7,036,946 | B1 | 5/2006 | Mosier |
| 9,075,907 | B2 | 7/2015 | Fujimoto |
| 9,703,171 | B2 | 7/2017 | Zhou et al. |
| 11,137,953 | B2 | 10/2021 | Ohmura |
| 11,800,990 | B2 | 10/2023 | White et al. |
| 12,002,572 | B2 | 6/2024 | Beechem et al. |
| 2003/0007598 | A1* | 1/2003 | Wang ............ A61B 6/463 378/37 |
| 2006/0161287 | A1 | 7/2006 | Simonis |
| 2009/0086316 | A1 | 4/2009 | Kawahito |
| 2013/0260382 | A1 | 10/2013 | Ghosh et al. |
| 2015/0219979 | A1 | 8/2015 | Zhou et al. |
| 2015/0378143 | A1 | 12/2015 | Auguste |
| 2016/0209635 | A1 | 7/2016 | Yan |
| 2016/0314583 | A1* | 10/2016 | Couch ............ H04N 23/56 |
| 2017/0016909 | A1 | 1/2017 | Beechem et al. |
| 2017/0262984 | A1* | 9/2017 | Barnes ............ G06V 20/698 |
| 2017/0309021 | A1 | 10/2017 | Barnes et al. |
| 2018/0330510 | A1 | 11/2018 | Watanabe |
| 2019/0236780 | A1* | 8/2019 | Barnes ............ G06T 7/0012 |
| 2020/0080060 | A1 | 3/2020 | Matheu et al. |
| 2020/0097727 | A1* | 3/2020 | Stumpe ............ G02B 21/361 |
| 2022/0076809 | A1 | 3/2022 | Beechem et al. |
| 2023/0081232 | A1* | 3/2023 | Weisenfeld ........ G06V 20/69 382/133 |
| 2023/0238078 | A1* | 7/2023 | Gonzalez Lozano ........... G06T 7/0012 382/128 |
| 2024/0347176 | A1 | 10/2024 | Beechem et al. |

FOREIGN PATENT DOCUMENTS

| | | |
|---|---|---|
| CN | 101738618 A | 6/2010 |
| CN | 101915615 A | 12/2010 |
| CN | 201837458 U | 5/2011 |
| CN | 102564590 A | 7/2012 |
| CN | 103149180 A | 6/2013 |
| CN | 103743485 A | 4/2014 |
| CN | 103913419 A | 7/2014 |
| CN | 205403956 U | 7/2016 |
| CN | 106017680 A | 10/2016 |
| CN | 106352978 A | 1/2017 |
| CN | 107589078 A | 1/2018 |
| CN | 107850768 A | 3/2018 |
| CN | 108225282 A | 6/2018 |
| CN | 108332855 A | 7/2018 |
| JP | 2003241108 A | 8/2003 |
| JP | 2008009298 A | 1/2008 |
| JP | 2008501436 A | 1/2008 |
| JP | 2008206969 A | 9/2008 |
| JP | 2016526687 A | 9/2016 |
| JP | 2017092730 A | 5/2017 |
| JP | 2017191287 A | 10/2017 |
| JP | 2018503906 A | 2/2018 |
| JP | 2018031890 A | 3/2018 |
| JP | 2018529314 A | 10/2018 |
| WO | WO-2005117711 A2 | 12/2005 |
| WO | WO-2013024600 A1 | 2/2013 |
| WO | WO-2016107896 A1 | 7/2016 |
| WO | WO-2017015097 A1 | 1/2017 |
| WO | WO-2017015099 A1 | 1/2017 |
| WO | WO-2018218085 A2 | 11/2018 |
| WO | WO-2018231204 A1 | 12/2018 |
| WO | WO-2020132577 A1 | 6/2020 |
| WO | WO-2021076928 A1 | 4/2021 |

OTHER PUBLICATIONS

Amaria, R. N., et al., "Neoadjuvant immune checkpoint blockade in high-risk resectable melanoma", Nature Medicine (2018); 24(11): 1649-1654.

[Author Unknown] "Distribution of In Vitro Diagnostic Products Labeled for Research Use Only or Investigational Use Only", Food and Drug Administration (Nov. 25, 2013) [online] https://www.fda.gov/downloads/MedicalDevices/DeviceRegulationandGuidance/Guida nceDocuments/ucm376118.pdf; 12 pages.

[Author Unknown] "GeoMx Digital Spatial Profiler Data Analysis User Manual", NanoString Technologies, Inc. (Jun. 2019); 84 pages.

[Author Unknown] "GeoMx™ Digital Spatial Profiler", NanoString Technologies, Inc. (Feb. 2019); 7 pages.

[Author Unknown] "nCounter® Analysis System User Manual", MAN-C0035-07 96, NanoString Technologies, Inc. (Jul. 2018); 96 pages.

Buchanan, K., et al., "Unlocking Predictive Potential for Response to Immunotherapy Digital Spatial Profiling Technology", NanoString Technologies®, Inc. (Mar. 2019); 8 pages.

Cesano, A., et al., "Abstract 1371: Spatially-resolved, multiplexed digital characterization of protein distribution and abundance in FFPE tissue sections", AACR 107th Annual Meeting (Apr. 16-20, 2016); 5 pages; doi.org/10.1158/1538-7445.AM2016-1371.

Chen, P. C., et al., "An Augmented Reality Microscope for Real-time Automated Detection of Cancer", Google AI Healthcare, Google, Inc. (Apr. 16, 2018); 21 pages with Supplementary Data.

Chenn, A., "Wnt/B-catenin signaling in cerebral cortical development", Organogenesis (2008); 4(2): 76-80.

Dubeau, L., et al., "Southern Blot Analysis of DNA Extracted from Formalin-fixed Pathology Specimens", Cancer Research (1986); 46(6): 2964-2969.

Eggermont, A. M. M., et al., "Prolonged survival in stage III melanoma with ipilimumab adjuvant therapy", New England Journal of Medicine (2016); 375(19): 1845-1855.

Goyal, A., et al., "S100b as a Prognostic Biomarker in Outcome Prediction for Patients with Severe Traumatic Brain Injury", Journal of Neurotrauma (2013); 30(11): 946-957.

Jeong, H., et al., "Brain Inflammation and Microglia: Facts and Misconceptions", Experimental Neurobiology (2013); 22(2): 59-67.

Mallory, F. B., "The Results of the Application of Special Histological Methods to the Study of Tumors", The Journal of Experimental Medicine (1908); 10(5): 575-593.

Misharin, A. V., et al., "Flow Cytometric Analysis of Macrophages and Dendritic Cell Subsets in the Mouse Lung", American Journal of Respiratory Cell and Molecular Biology (2013); 49(4): 503-510.

Müller, A. M., et al., "Expression of CD34 in Pulmonary Endothelial Cells in vivo", Pathobiology (2002); 70(1): 11-17.

Mudanyali, O., et al., "Integrated rapid-diagnostic-test reader platform on a cellphone", Lab Chip (2012); 12: 2678-2686.

Walter, P. R., "Placental pathologic changes in malaria. A histologic and ultrastructural study", The American Journal of Pathology (1982); 109(3): 330-342.

(56) References Cited

OTHER PUBLICATIONS

Weber, J., et al., "Adjuvant nivolumab versus ipilimumab in resected stage III or IV melanoma", New England Journal of Medicine (2017); 377(19): 1824-1835.

Wiolchok, J. D., et al., "Overall Survival with Combined Nivolumab and Ipilimumab in Advanced Melanoma", New England Journal of Medicine (2017); 377(14): 1345-1356.

Xu, X., et al., "S100A9 promotes human lung fibroblast cells activation through receptor for advanced glycation end-product-mediated extracellular-regulated kinase 1/2, mitogen-activated protein-kinase and nuclear factor-κB-dependent pathways", Clinical and Experimental Immunology (2013); 173(3): 523-535.

\* cited by examiner

SYSTEMS AND METHODS FOR SPATIAL MAPPING OF EXPRESSION PROFILING

RELATED APPLICATIONS

This application is a U.S. National Phase application, filed under 35 U.S.C. § 371, of International Application No. PCT/US2020/056035, filed Oct. 16, 2020, which claims benefit of and priority to U.S. provisional patent application No. 62/916,990, filed Oct. 18, 2019, the entire contents of which are herein incorporated by reference in their entireties.

FIELD OF INVENTION

The present disclosure relates to systems, apparatuses, and methods for visual-spatial resolution and digital quantification of protein and mRNA expression.

BACKGROUND

Diseases such as cancer involve abnormal cell growth, with such abnormal growth generally resulting in one or more tumors either localized or metastasized around the body. Surgery is the first line of treatment to remove tumors, cancerous lymph nodes, and healthy tissue adjacent to the tumors. Often adjuvant therapy is administered post-surgery, which can include weeks of radiation, chemotherapy, targeted drug therapy, and/or immunotherapy. These therapies can have mixed outcomes and side effects that vary by patient. Researchers are actively investigating the differences in outcomes so as to identify biomarkers that may predict a patient's response to treatment. These expression signatures may help guide the physician to administer more effective treatments in a deliberate, evidence-based manner.

The challenge today is in identifying the biomarkers at play in the tumor microenvironment. However, such biomarkers in a tumor sample often requires destroying the tissue, which most often sacrifices spatial information about the biomarkers. Although fluorescence and bright-field imaging can provide a visual map of the biomarkers, they are limited by the number of fluorophores that can be captured in one experiment, requiring multiple rounds of immunostaining and imaging on the same sample. This can results in the sample degrading over time and leading to errors in image registration and misinterpretation of results.

Accordingly, there is a need for a solution by which to overcome the aforementioned problems, such as those associated with the identification and characterization of biomarkers and combinations thereof which are at play in the tumor microenvironment, so as to improve immunohistochemical systems, methods, and techniques such that more reliable and effective treatments may be administered in a more deliberate, evidence-based manner.

SUMMARY OF SOME OF THE EMBODIMENTS

Accordingly, in some embodiments, a biological expression mapping system and method configured to spatially map one or more biological expressions of respective target biological components contained in a tissue sample to an image of the tissue sample is provided.

One of skill in the art will appreciate that system embodiments which detail various computer instructions operating/operational on one or more processors (e.g., servers, personal computers) to cause such one or more processors (e.g., system) to perform various processing steps, can be steps for one or more mapping method embodiments in the present disclosure.

Accordingly, in some embodiments, the system includes at least one processor having instructions operational thereon that, when executed, are configured to cause the system to display, in a first display, a scans pane which includes at least the image of the tissue sample, the image including one or more demarcations each corresponding to a particular one of one or more regions-of-interest (ROIs), each of the one or more ROIs corresponding to a specific portion of the tissue within the tissue image. The instructions are further configured to cause the system to display, in a second display, a visualization pane comprising a visualization of each of the respective biological expressions contained in the one or more ROIs. The instructions are further configured to cause the system to augment the first display by coding the one or more ROIs in the tissue image to show the spatial mapping of the biological expressions within the one or more ROIs.

In some embodiments, a biological expression mapping method is provided, and includes displaying, in a first display, a scans pane which includes at least the image of the tissue sample, the image including one or more demarcations each corresponding to a particular one of one or more regions-of-interest (ROIs), each of the one or more ROIs corresponding to a specific portion of the tissue within the tissue image, displaying, in a second display, a visualization pane comprising a visualization of each of the respective biological expressions contained in the one or more ROIs, and augmenting the first display or the second display by coding the one or more ROIs in the tissue image to show the spatial mapping of the biological expressions within the one or more ROIs.

Each of the embodiments noted above (i.e., systems, methods) can further include at least one of (and in some embodiments, a plurality of, and in some embodiments substantially all of) the following additional structures, features, steps, functionalities, and/or clarifications, yielding yet additional embodiments (moreover, each of the items in the listing below, and combinations of the items listed below can be stand-alone embodiments):

- coding comprises at least color-coding;
- the visualization of each of the respective biological expressions includes an image of a biological expression contained in an ROI of the one or more ROIs;
- the graph, the plot, the diagram, and the map of the biological expressions comprise at least one of a heatmap, a tree diagram, a bar chart, a scatter plot, a box plot, a forest plot, a principal component, a statistical plot, a volcano plot, a trend plot, and a strip plot;
- the tree diagram includes a dendrogram;
- the statistical plot includes one or more principal component analysis (PCA) plots;
- the first display is augmented based upon user input specifying at least one selection of a biological expression contained in the visualization;
- the spatial mapping of the at least one user selected biological expression is configured to provide spatial context thereof to at least one of the one or more of the ROIs;
- augmenting the first display is configured to facilitate morphological profiling of tissue in at least one of the one or more ROIs;
- morphological profiling comprises at least one of geometric profiling, segment profiling, contour profiling, gridded profiling, and cell profiling;

segment profiling comprises at least one of manual segment profiling and automatic segment profiling, the automatic segment profiling configured to automate and facilitate segment profiling of tissue in at least one of the one or more ROIs based on user input specifying at least one segment profiling parameter;

cell profiling comprises single cell profiling and rare cell profiling;

the one or more biological expressions of the respective one or more target biological components at least within the one or more ROIs are determined based upon exposing the tissue sample to a plurality of reagents, and the reagents include:
  a plurality of imaging reagents configured to bind to biological boundaries of the tissue sample within at least the one or more ROIs, and
  a plurality of profiling reagents, each profiling reagent is configured to:
    bind to a specific biological expression of a specific target biological component contained within at least the one or more ROIs, and
    include a cleavable, associated oligonucleotide;

after exposing the tissue sample to the plurality of reagents, and prior to displaying in the first display and the second display, the instructions are further configured to cause the system to (or the method further comprises):
  illuminate and image the tissue sample;
  receive user input specifying a selection of the one or more ROIs;
  irradiate the tissue sample at least at one or more of the ROIs to thereby cleave the associated oligonucleotides from the profiling reagents;
  collect the cleaved oligonucleotides; and
  analyze the collected, cleaved associated oligonucleotides to determine:
    the one or more biological expressions contained within at least the one or more ROIs, and
    their corresponding location therein;

each profiling reagent comprises:
  a nucleic acid probe including a target binding region in which the cleavable, associated oligonucleotide is removably linked; or
  an oligonucleotide including a removably linked antibody:

the user input specifying the selection of the one or more ROIs includes a selection of one or more of the ROIs with respect to shape or size;

the instructions are further configured to cause the system to (or the method further includes):
  display, in a third display, a datasets pane which includes at least one user-selectable dataset, the at least one dataset associated with one or more of the biological expressions contained in the one or more ROIs;

the instructions are further configured to cause the system to (or the method further includes):
  display, in a fourth display, a records pane which includes a plurality of scanning records, each containing at least one tissue image:

one or more of the first display, the second display, the third display, and the fourth display are provided within a unified user interface configured to interactively associate, based on user input, one or more of the tissue image, the visualizations, the user-selectable datasets, and one or more of the plurality of scanning records;

the unified user interface is configured as a single display;

the first display, the second display, the third display, and the fourth display respectively correspond to one or more portions of the single display;

the instructions are further configured to cause the system to (or the method further includes):
  select, based on user input, at least one record, such that, upon selection thereof, at least one of the scans pane, the visualization pane, and the datasets pane is displayed in a respective display;

the instructions are further configured to cause the system to (or the method further includes) filter, based on user input, at least one of a property, a constraint, and a value for the plurality of records;

the scans pane further includes a plurality of icons each corresponding to a specific segment within at least one of the one or more ROIs or the overall tissue image;

the instructions are further configured to cause the system to (or the method further includes) render, for display via the unified user interface and in real-time based on user input, the scans pane in conjunction with the visualization pane and one or more of the datasets pane and the records pane;

coding the one or more ROIs includes presenting a quantitative measurement of the biological expressions;

color-coding the one or more ROIs includes presenting a quantitative measurement of the biological expressions;

the quantitative measurement corresponds to at least one of a type and degree of respective biological expressions;

the quantitative measurement corresponds to at least one of a type and degree of respective biological expressions; and the type or degree corresponds to a particular color for each respective biological expression or an intensity of a color for each respective biological expression.

Embodiments of the present disclosure are also related to PCT application no. PCT/US2016/042460 (WO2017/015099), filed 15 Jul. 2016, entitled, "SIMULTANEOUS QUANTIFICATION OF GENE EXPRESSION IN A USER-DEFINED REGION OF A CROSS-SECTIONED TISSUE", and PCT application no. PCT/US2016/042455 (WO 2017/015097), filed 15 Jul. 2016, entitled, "SIMULTANEOUS QUANTIFICATION OF PLURALITY OF PROTEINS IN A USER-DEFINED REGION OF A CROSS-SECTIONED TISSUE", the disclosures of which are each incorporated herein by reference in their entirety.

The above note embodiments, as well as other embodiments, and objects and advantages thereof, will become even more apparent with reference to the figures, a brief description of which his set out below, and the following detailed description (of at least some of the embodiments).

DETAILED DESCRIPTION FOR AT LEAST SOME OF THE EMBODIMENTS

Embodiments of the present disclosure are directed to devices, systems, and methods for analyzing biological matter, by spatial resolution and digital quantification of discrete occurrences of gene expression ("gene expression(s)" or "expression event(s)") in and of the matter. Expression events can include, for example, protein expression, mRNA expression, and the like. In some instances, the biological matter can include, for example, a sample such as a tissue sample (e.g., slide-mounted, formalin fixed paraffin-embedded (FFPE) tissue section), a lysate, a biological fluid sample, and the like ("biological matter" or "sample" or "tissue sample"). The sample can comprise tissue (e.g., including cultured or explanted), as well as cells which make up such tissue (e.g., including both primary cells and cultured cell lines). For instance, the sample can include:
 a cultured cell, a primary cell, or a dissociated cell (e.g., from an explant);
 biological matter such as a tissue, user-defined cell, and/or user-defined subcellular structure within a cell;
 a tissue section having a thickness of approximately 2 to 1000 micrometers (μm);
 and
 cultured cells or dissociated cells (fixed or unfixed) that have been immobilized onto a slide.

Advantageously, some embodiments of the present disclosure enable efficient characterization of tissue heterogeneity, which can be critical to answering key biological questions in translational research. The current tissue analysis paradigm requires a tradeoff between morphological analysis or high-plex, sacrificing valuable information or consuming precious samples. To this end, in some embodiments, generation of a whole tissue image at single cell resolution and digital profiling data for 10's-1,000's of RNA or Protein analytes for up to 16-20 tissue slides per day are possible. This unique combination of high-plex, high-throughput spatial profiling can enable researchers to rapidly and quantitatively assess the biological implications of the heterogeneity within tissue samples. Moreover, some embodiments of the present disclosure enable high-plex, high-throughput, multi-analyte, and non-destructive characterization of tissue samples.

Figure 1:
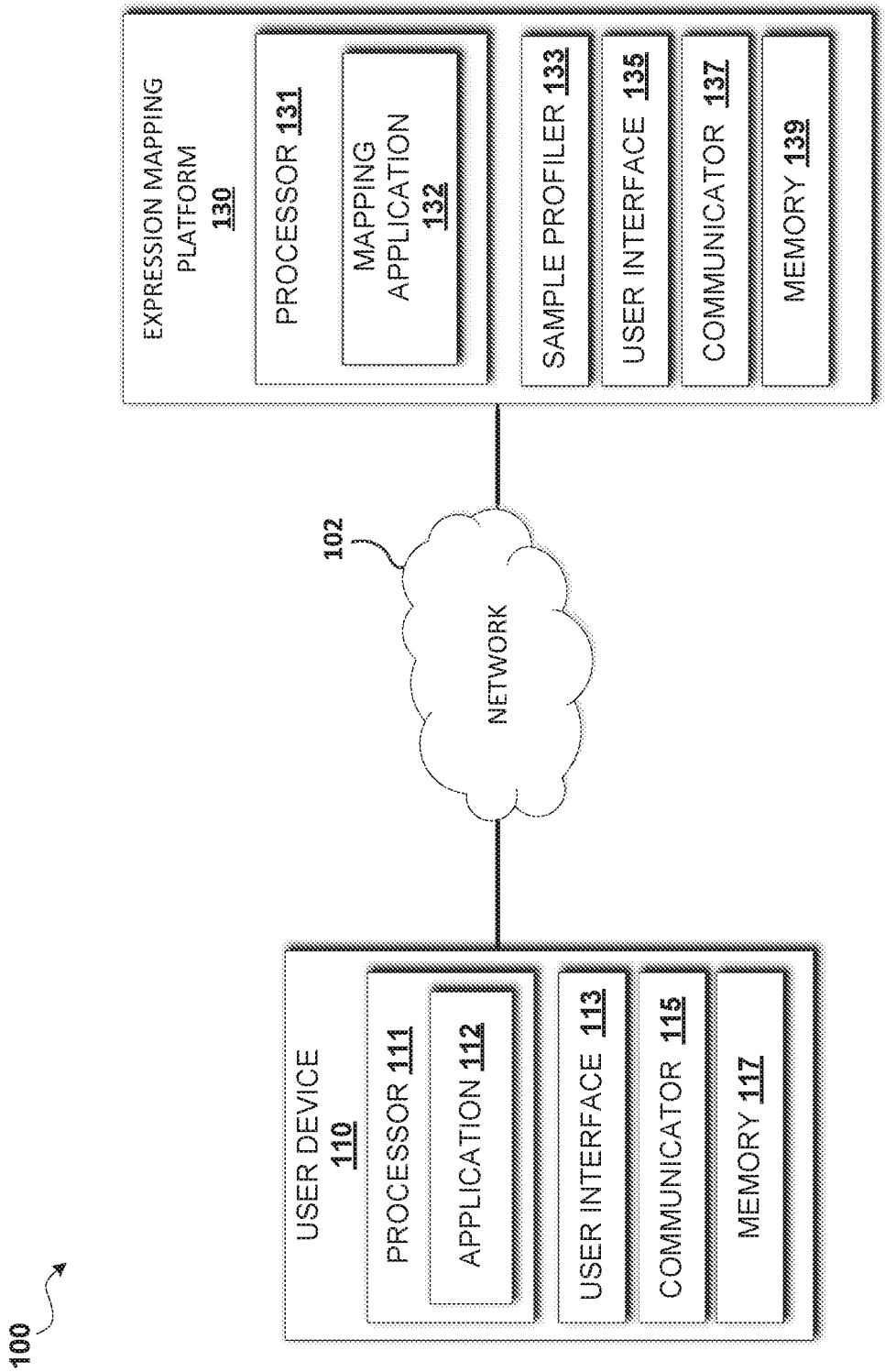
FIG. 1 is a functional block diagram depicting an expression mapping system, in accordance with some embodiments of the present disclosure.

FIG. 1 is a schematic block diagram depicting expression mapping system 100, according to some embodiments. As shown, expression mapping system 100 can include user device 110 and expression mapping platform 130, interconnected over network 102. While expression mapping system 100 is shown as including two discrete devices, other arrangements can be contemplated. For example, in other embodiments, instead of including at least five discrete components (e.g., 131, 133, 135, 137, 139), expression mapping platform 130 can include, for example, at least four discrete components (e.g., 131, 133, 135, 139). Moreover, one and/or another of the functionalities of the various components of the user device and mapping platform can be combined into a single device/system.

Network 102 can be or include, for example, an intranet, a local area network (LAN), a personal area network (PAN), a wireless local area network (WLAN), a wireless personal area network (WPAN), a wide area network (WAN) such as the Internet, a metropolitan area network (MAN), a world-wide interoperability for microwave access network (WiMAX®), an optical fiber (or fiber optic)-based network, a Wi-Fi™ network, a Bluetooth® network, a virtual network, and/or any combination thereof. Network 102 can include, for example, wired connections, wireless (e.g., radio communication, free-space optical communication) connections, fiber optic connections, and the like. Network 102 can include, for example, routers, firewalls, switches, gateway computers, edge servers, and the like. In some instances, network 102 can alternatively or otherwise include, for example, telecommunications, data communications, and/or data transmission channel, link, connection, or path, by which data and signals can be communicated, transmitted, or propagated between and amongst devices. For example, network 102 can include a near-field communications (NFC) connection (e.g., NFC beacon connection), a short-range or short-link communications connection (e.g., Bluetooth®), and/or the like. Network 102 can include any suitable combination of connections and protocols configured to enable and support interconnection, communications, and interoperations between user device 110 and expression mapping platform 130.

User device 110 and expression mapping platform 130 can individually and respectively include, for example, a device, node, system, or platform, such as a machine or compute device, compute system, compute platform, information system, programmable electronic device, information content processing device, and/or the like. For example, user device 110 and/or expression mapping platform 130 can include, for example, a controller, a processor, a mobile phone, a smart phone, a tablet computer, a laptop computer, a personal or desktop computer, a server (e.g., database server), a virtual machine, a wearable device (e.g., electronic watch), an implantable device, and/or the like. User device 110 and/or expression mapping platform 130 can otherwise be, include, or use any suitable type and combination of devices, systems, and/or platforms, capable of communicating or interoperating (e.g., via network 102) with one or more other devices, systems, and/or platforms, such as user device 110 and/or expression mapping platform 130. In some embodiments, user device 110 and/or expression mapping platform 130 may include internal and external hardware components, such as described with reference to FIG. 9. In other embodiments, user device 110 and/or expression mapping platform 130 may be implemented in a cloud computing environment, such as described with reference to FIGS. 10 and 11.

User device 110 includes processor 111, user interface 113, communicator 115, and memory 117. User device 110 can be configured to implement any suitable combination of devices and technologies, such as network devices and device drivers, to support the operation of processor 111, user interface 113, communicator 115, and memory 117, and provide a platform enabling communications (e.g., via network 102) between user device 110 and expression mapping platform 130.

Processor 111 can be or include any suitable type of processing device configured to run and/or execute software, code, commands, or logic. For example, processor 111 can be or include a hardware-based integrated circuit (IC), a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC), or the like. Processor 111 can be operatively coupled to memory 117, such as by way of a data transfer device or system such as a bus (e.g., address bus, data bus, control bus). Processor 111 can otherwise include a processor configured to execute any suitable type or form of software, code, commands, and/or logic, corresponding to or representative of an application or program such as application 112, as described herein.

Application 112 can be or include any suitable type of application or program, such as a software or computer program, one or more subroutines contained in a program, an application programming interface, or the like. Application 112 can include any suitable type or form of software, code, commands, and/or logic representing instructions, such as machine-, computer-, or processor-executable code, logic, instructions, commands, and/or the like. Application 112 can be configured to reside or be hosted at user device 110. For example, application 112 can be configured to be stored (e.g., via memory 117) at user device 110. Alternatively or in combination, application 112 can be configured to reside or be hosted at a device separate, distinct, or remote from user device 110, such as at a server, node, and/or the like. Application 112 can be configured to be run or executed by, at, or via any suitable type of processor or processing device, such as processor 111. For example, application 112 can be or include a native application, a web or web-based application, and/or a hybrid application (e.g., an application having a combination of native and web-based application characteristics or functionality).

User interface 113 can be or include any suitable type of user interface device configured to enable user interaction between a user and user device 110. In some embodiments, user interface 113 can be configured to enable user interaction between user (e.g., at user device 110) and expression mapping platform 130, as described herein. For example, user interface 113 can be configured to provide (e.g., display) output (e.g., from mapping application 132 and/or from sampling profiler 133). Further, user interface 113 can be configured to receive user input (e.g., from a user at user device 110), as described herein. For example, user interface 113 can include one or more input devices such as a keyboard and mouse, and one or more output devices such as displays, screens, projectors, and the like. As another example, user interface 113 can include one or more input/output (I/O) devices, such as a touchscreen, a holographic display, a wearable device such as a contact lens display, an optical head-mounted display, a virtual reality display, an augmented reality display, and/or the like. User interface 113 can be configured to implement any suitable type of human-machine interface device, human-computer interface device, a batch interface, graphical user interface (GUI), and the like. User interface 113 can otherwise include or be configured to implement any suitable type of interface (e.g., user interface 113) capable of embodiment in conjunction with a device such as expression mapping platform 130, such as to provide for user interaction between a user and the device, as described herein. In some embodiments, the user input received at user interface 113 can be sent (e.g., over network 102) to expression mapping platform 130 for execution thereat.

Communicator 115 can be or include, for example, a hardware device operatively coupled to processor 111 and memory 117, and/or software stored in memory 117 and executable by processor 111, capable of enabling and supporting communications over a network (e.g., network 102) and/or directly between or among compute devices (e.g., user device 110 and expression mapping platform 130). For example, communicator 115 can be or include a network interface card (NIC), a network adapter such as a Transmission Control Protocol (TCP)/Internet Protocol (IP) adapter card or wireless communication adapter (e.g., a 4G wireless communication adapter using Orthogonal Frequency Division Multiple Access (OFDMA) technology), a Wi-Fi™ device or module, a Bluetooth® device or module, and/or any other suitable wired and/or wireless communication device. Communicator 115 can be configured to connect or interconnect user device 110 and one or more other devices (e.g., expression mapping platform 130) for data communications therebetween, such as over a communications network (e.g., network 102). Communicator 115 can be configured to be implemented in conjunction with any suitable architecture, such as one designed for passing data and/or control information between processors (e.g., processor 111, processor 131), system memory (e.g., memory 117, memory 139), peripheral devices (e.g., user interface 113, user interface 135), and any other devices or components (e.g., of expression mapping system 100 and/or including expression mapping platform 130) within a system such as an expression mapping system (e.g., expression mapping system 100), as described herein.

Memory 117 can be or include any suitable type of memory, data storage, or machine-computer-, or processor-readable media capable of storing a machine or computer program, digital information, electronic information, and the like (e.g., of or associated with application 112). For example, memory 117 can be configured to store an application or program such as application 112, such as for execution by processor 111. Memory 117 can be or include a memory buffer, a hard drive, a magnetic disk storage device of an internal hard drive, magnetic tape, magnetic disk, optical disk, portable memory (e.g., flash drive, flash memory, portable hard disk, memory stick), a semiconductor storage device such as a random access memory (RAM) (e.g., RAM including cache memory), a read-only memory (ROM), an erasable programmable read-only memory (EPROM), an electrically erasable programmable read-only memory (EEPROM), and/or the like. Memory 117 can otherwise include any suitable type of memory or data storage, as such may be chosen as a matter of design.

Expression mapping platform 130 includes processor 131, sample profiler 133, user interface 135, communicator 137, and memory 139. Expression mapping platform 130 can be configured to implement any suitable combination of devices and technologies, such as network devices and device drivers, to support the operation of processor 131, sample profiler 133, user interface 135, communicator 137, and memory 139, and provide a platform enabling communications (e.g., via network 102) between user device 110 and expression mapping platform 130, as described herein. Expression mapping platform 130 can be configured to spatially map (e.g., via sample profiler 133) one or more biological expressions of respective target biological components contained in a tissue sample to an image of the tissue sample, as described herein. While expression mapping platform 130 is shown as including five discrete elements or components (e.g., processor 131, sample profiler 133, user interface 135, communicator 137, memory 139), other arrangements can be contemplated. For example, in some embodiments, expression mapping platform 130 can alternatively or otherwise include processor 131, sample profiler 133, user interface 135, and memory 139 (e.g., four discrete elements or components), and/or any other number of discrete elements or components (e.g., including one or more integrated or separate devices, platforms, nodes, etc.), as such may be chosen as a matter of design.

In some embodiments, the expression mapping platform 130 can comprise a device, system, or platform such as a biological expression mapping system, a biological tissue or matter imaging system, a gene expression analysis device, a gene expression imaging device, a gene expression profiling device, a gene expression mapping device, a digital spatial profiling device, a molecular imaging device, and the like (collectively, "expression mapping platform"). For example, in some instances, expression mapping platform 130 can include one or more nCounter® systems and/or methods from NanoString Technologies® (South Lake Union in Seattle, Washington), as described herein.

Processor 131 can be or include any suitable type of processing device configured to run and/or execute software, code, commands, or logic. For example, processor 131 can be or include a hardware-based integrated circuit (IC), a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC), or the like. Processor 131 can be operatively coupled to memory 139, such as by way of a data transfer device or system such as a bus (e.g., address bus, data bus, control bus). Processor 131 can otherwise include a processor configured to execute any suitable type or form of software, code, commands, and/or logic, corresponding to or representative of an application or program such as mapping application 132, as described herein.

Mapping application 132 can be or include any suitable type of application or program, such as a software or computer program, one or more subroutines contained in a program, an application programming interface, or the like. Mapping application 132 can include any suitable type or form of software, code, commands, and/or logic representing instructions, such as machine-, computer-, or processor-executable code, logic, instructions, commands, and/or the like. In some embodiments, mapping application 132 can be configured to communicate with sample profiler 133, as described herein. Mapping application 132 can be configured to reside or be hosted at expression mapping platform 130. For example, mapping application 132 can be configured be stored (e.g., via memory 139) at expression mapping platform 130. Alternatively or in combination, mapping application 132 can be configured to reside or be hosted at a device separate, distinct, or remote from expression mapping platform 130, such as at a server, node, device, and/or the like. Mapping application 132 can be configured to be run or executed by, at, or via any suitable type of processor or processing device, such as processor 131. For example, mapping application 132 can be or include a native application, a web or web-based application, and/or a hybrid application (e.g., an application having a combination of native and web-based application characteristics or functionality).

In some embodiments, mapping application 132 can be configured to control, based on user input, an operation of expression mapping platform 130 such as by communicating executable commands and/or instructions (e.g., corresponding to the user input) to sample profiler 133. For example, mapping application 132 can be configured to receive (e.g., from a user at user interface 135 and/or user interface 113) user input corresponding to the instructions, and to send corresponding instructions based on the user input ("user input instructions") to sample profiler 133 to thereby cause sample profiler 133 to perform various operations. For example, the user input instructions, when executed, can be configured to cause sample profiler 133 to load a sample, to identify information for association with the sample, to scan the sample to generate a corresponding image (e.g., fluorescent image) of the sample, to determine a user-input based selection specifying one or more ROIs with respect to the sample, among other associated operations, as described herein. An ROI may be or include, for example, a tissue type present in a sample, a cell type, a cell, or a subcellular structure within a cell.

In some embodiments, sample profiler 133 represents a device or system configured to at least one of:
 image and analyze a sample;
 spatially map one or more biological expressions of respective target biological components contained in a tissue sample to an image of the sample; and
 perform or implement multiplexed detection, analysis, and/or quantification of expression events (e.g., protein expression, mRNA expression) in a user-defined region of a sample (e.g., one or more ROIs).

For example, sample profiler 133 can be configured to spatially map, based on instructions corresponding to user input specifying a selection of one or more ROIs (e.g., received via mapping application 132 and from a user at user device 110 or expression mapping platform 130), one or more biological expressions of respective target biological components contained in the sample (at the one or more ROIs) to the image of the sample, as described herein.

In some embodiments, sample profiler 133 can include, for example, a sample preparation station (not shown) and an analysis instrument (not shown). The analysis instrument can include, for example, a digital analysis instrument ("digital analyzer"). For example, sample profiler 133 can include, for example, the GeoMx® Digital Spatial Profiler (DSP) from NanoString Technologies®. In this example, the sample preparation station and the digital analyzer can include an nCounter® Prep Station and an nCounter®, digital analyzer, respectively. In some embodiments, sample profiler 133 can be configured to receive a sample such as a tissue sample for processing, for and prior to data collection (e.g., via the sample preparation station), and to subsequently perform data collection and analysis (e.g., via the digital analyzer) on the processed tissue sample, as described herein. In some embodiments, sample profiler 133 can be controlled or otherwise configured to be implemented based on user input instructions corresponding to user input received via mapping application 132 and/or a user interface (e.g., user interface 113, user interface 135) as described herein.

In some embodiments, the sample preparation station can include, for example, an automated sample preparation station such as a multi-channel pipetting robot, configured to process one or more samples (e.g., labeled tissue, user-defined cell, user-defined subcellular structure within a cell) for subsequent data collection and analysis (e.g., via the digital analyzer), as described herein. In some embodiments, processing one or more of the samples can include, for example, preparing a sample by staining, or exposing the sample to a plurality of reagents (e.g., hybridization). For example, the sample preparation station can be configured to process a sample for subsequent data collection and analysis (e.g., via the digital analyzer) by staining or labeling the one or more samples to thereby enable visualization of a subcellular or cellular structure in the stained or labeled cell, such as in the case of a sample that includes at least one cell; or, alternatively or in addition, to thereby enable visualization of a subcellular, cellular, or tissue-related structure or section in the stained or labeled tissue sample, such as in the case of sample that includes a tissue sample.

The plurality of reagents can include, for example, a plurality of imaging reagents and plurality of profiling reagents. In some embodiments, the plurality of imaging reagents can include, for example, one or more markers, tags, and the like. For example, in some instances, the plurality of imaging reagents can include one or more imaging reagents such as a fluorescent morphology marker (e.g., up to four). In some embodiments, the plurality of profiling reagents can include, for example, one or more RNA and/or protein detection reagents, or probes ("profiling reagent(s)" or "probe(s)"). For example, the plurality of profiling reagents can include between about 10 and 10,000 profiling reagents. Each protein detection reagent, or probe, can include, for example, a cleavable probe such as a photo-cleavable (e.g., UV-cleavable) probe, and the like. In some embodiments, a probe can include two or more labeled oligonucleotides per antibody. For example, each probe can include a target-binding domain and a signal oligonucleotide. The target-binding domain can include, for example, a protein-binding molecule (e.g., antibody, peptide, aptamer, peptoid). The signal oligonucleotide can include, for example, a single-stranded nucleic acid or a partially double-stranded nucleic acid.

In some embodiments, each imaging reagent can be configured to bind to biological boundaries of the tissue sample within at least the one or more ROIs, and each profiling reagent can be configured to bind to a specific biological expression of a specific target biological component contained within at least the one or more ROIs. In some embodiments, each profiling reagent can further be configured to include, for example, a cleavable, associated oligonucleotide, and in some embodiments, each profiling reagent can include, for example, one or more of a nucleic acid probe including a target binding region in which the cleavable, associated oligonucleotide is removably linked, or an oligonucleotide including a removably linked antibody. In some embodiments, the removable linkage can include, for example, a linker (e.g., a cleavable linker) located between the target-binding domain and the signal oligonucleotide. The cleavable linker can include, for example, a photocleavable linker configured to be cleaved by electromagnetic radiation (e.g., light) emitted by a light source, such as a suitable coherent light source (e.g., laser, laser scanning device, confocal laser scanning device, UV light source) or a suitable incoherent light source (e.g., an arc-lamp and a light-emitting diode (LED)). In some embodiments, the light source can additionally or otherwise include, for example, a digital mirror device (DMD).

In some embodiments, the cleavable, associated oligonucleotide can include, for example, a photocleavable oligonucleotide tag. For example, the tissue sample can be prepared for the assay (e.g., via expression mapping platform 130) by using antibody or RNA probes coupled to photocleavable oligonucleotide tags. In some embodiments, each photocleavable oligonucleotide tag can be or include a machine-readable identifier which can be scanned or read by a scanner, such as a barcode scanner, and the like. In some instances, the photocleavable oligonucleotide tags can be bound with one or more morphology markers, to slide-mounted FFPE tissue sections. In some embodiments, the one or more morphology markers can include, for example, up to four morphology markers, where each morphology marker can include, for example, a fluorescent probe. After the binding of the oligoconjugated probes and the morphology markers to the slide-mounted FFPE tissue sections, the oligonucleotide tags can be released from selected regions of the tissue for further analysis.

In some embodiments, the sample preparation station can further be configured to perform other processing operations, including, for example, liquid transfer operations, magnetic bead separation operations, immobilization operations (e.g., of molecular labels on the sample cartridge surface), and the like. The sample can be fixed or unfixed. For example, in some instances, sample processing via the sample preparation station can include purification and immobilization of a sample including at least one cell onto a surface (e.g., internal surface) of a container (e.g., sample container), cartridge (e.g., sample cartridge), and/or the like. For example, at least one cell can be directly immobilized to a surface or can be indirectly immobilized to the surface via at least one other cell. After processing of the tissue sample, sample profiler 133 can be configured to transfer the tissue sample to the digital analyzer for imaging, data collection, and analysis, as described herein.

In some embodiments, the digital analyzer can include, for example, a multiplexed analysis device, a scanner, a reading device, a counting device, and the like. For example, the digital analyzer can include a barcode scanning device, a multi-channel epifluorescence scanner, and the like. The digital analyzer can include an image capture device such as a charged-couple device (e.g., a camera), and a microscope objective lens. The digital analyzer can further include a transducer such as an energy source, energy emitter, light source, and the like ("light source"). In some embodiments, the light source can be or include, for example, a coherent light source (e.g., a LASER), an ultraviolet (UV) light source, and the like. In some embodiments, the light source can be or include, for example, an incoherent light source (e.g., arc-lamp and a light-emitting diode (LED)). The light source can be configured to irradiate, with respect to a sample, at least one subcellular structure of the at least one cell such that the abundance of the at least one protein target in or from the at least one subcellular structure of the at least one cell can be detected. Also, the light source may first irradiate at least one subcellular structure in the at least one cell and later irradiate at least one subcellular structure in the at least second cell, allowing a comparison of the abundance of the at least one protein target in or from the at least one subcellular structure in the at least one cell and the at least one subcellular structure in the at least second cell.

In some embodiments, the digital analyzer can be configured to determine one or more biological expressions contained within at least the one or more ROIs, as well as the corresponding locations thereof in the sample, so as to spatially map one or more of the biological expressions (e.g., of respective target biological components) contained in the sample, to the image of the sample. Accordingly, the digital analyzer can be configured to capture one or more images of a sample, collect, and/or analyze data associated with the sample, so as to spatially map one or more biological expressions of respective target biological components contained in the sample to the image of the sample. For example, the digital analyzer can be configured to count, quantitate, and/or quantify the biological expressions contained within at least one or more ROIs. Thus, in some embodiments, the digital analyzer can be configured to associate one or more mapped biological expressions with a visualization of each of the respective biological expressions contained in one or more ROIs.

Spatial mapping of the at least one user selected biological expression can be configured to provide spatial context between user selected biological expressions in the sample, and one or more associated ROIs (e.g., in which the user selected biological expression is positioned). In other words, spatial mapping of at least one user selected biological expression can be configured to provide spatial context thereof with respect to the tissue sample, between a biological expression of a target biological component (e.g., a position or location of occurrence of an expression event associated with or corresponding to the biological expression of the target biological component), and one or more ROIs (e.g., a position or location of occurrence of the one or more ROIs). In some embodiments, one or more biological expressions can be spatially mapped to the visualization or image of the tissue sample via spatial profiler 133, and as noted above, can be configured to count, quantitate, or quantify the biological expressions via the digital analyzer, as described herein.

In some embodiments, the digital analyzer can be configured to:
  contact at least one protein target in or from at least one cell in a tissue sample with at least one probe comprising a target-binding domain and a signal oligonucleotide;
  provide or apply a force to a location of the tissue sample sufficient to release the signal oligonucleotide; and
  collect and identify the released signal oligonucleotide, to thereby detect the at least one target in or from a specific location of the tissue sample that was provided the force, where the specific location can include, for example, a user-defined region of a tissue, user-defined cell, a user-defined subcellular structure within a cell, and the like (e.g., an ROI).

In some embodiments, the digital analyzer can be configured to repeat steps b) and c) on at least a second specific location of the tissue sample, the second specific location comprising at least a second cell. Detecting can include, for example, at least one of (and preferably a plurality of, and more preferably, all of):
  comparing the abundance of the at least one protein target in or from the first specific location and in or from the at least second specific location; the at least one cell and at least second cell may be the same cell type or distinct cell types;
  quantifying the abundance of the at least one protein target in or from a first cell type and in or from the at least a second cell type; and
  a polymerase reaction, a reverse transcriptase reaction, hybridization to an oligonucleotide microarray, mass spectrometry, hybridization to a fluorescent molecular beacon, a sequencing reaction, machine-reading of machine-readable identifiers such as nCounter® Molecular Barcodes, and the like.

In some embodiments, first and second cell types can be independently selected (e.g., based on input received at user interface 113 and/or user interface 135) from a normal cell and an abnormal cell, e.g., a diseased and cancerous cell.

In some embodiments, the target-binding domain comprises a protein-binding molecule, e.g., an antibody, a peptide, an aptamer, and a peptoid, and in some embodiments, two or more targets can be detected: e.g., between 1 and 1000 targets or more (e.g., corresponding to respective biological expressions), and any number therebetween. In some embodiments, the targets can respectively include or be associated with, for example, expression events associated with individual RNA targets, DNA targets, protein targets, and the like. In some embodiments, detecting can include, for example, quantifying the abundance of each target.

In some embodiments, the digital analyzer can be configured to illuminate (e.g., laser scanning device, DMD, etc.), and image a sample, to subsequently receive user input specifying a selection of one or more ROIs (e.g., based on the image of the sample), and to irradiate the tissue sample at least at one or more of the ROIs to thereby cleave the associated oligonucleotides from the profiling reagents. Further, in some embodiments, the digital analyzer can be configured to collect the cleaved oligonucleotides, and to analyze (e.g., quantitate) the collected, cleaved associated oligonucleotides to determine: the one or more biological expressions contained within at least the one or more ROIs, and their corresponding location therein. Accordingly, associated data from the digital analyzer can be output for use in generating an image and/or a visualization (e.g., corresponding to the spatial mapping of the one or more of the biological expressions and the image of the sample) for rendering or display (e.g., at user interface 113 and/or user interface 135) to provide for the spatial context, as described in further detail herein.

In some embodiments, the digital analyzer can be configured to generate the image and one or more associated, corresponding visualizations for display, viewing, and user interaction at a user interface (e.g., user interface 113, user interface 135), as described herein. For example, the digital analyzer can be configured to generate an image at single-cell resolution, and/or a visualization corresponding to measures (e.g., counts) of expression events, respectively associated with each of the respective biological expressions contained in one or more ROIs, such as described herein. In some embodiments, the visualization or image can include at least one of a graph, a plot, a diagram, and a map of the one or more biological expressions contained in the one or more ROIs, such as described herein with reference to FIGS. 3, 5, and 6A-I. The visualization or image of the tissue sample can be configured to facilitate morphological profiling, analysis, and characterization ("morphological profiling") of the tissue sample based on the biological expressions of respective target biological components contained in the tissue sample, and the locations of each biological expression in the tissue sample. In some embodiments, the morphological profiling can include, for example, at least one of geometric profiling, segment profiling, contour profiling, gridded profiling, and cell profiling, as described herein with reference to FIGS. 4A-E.

User interface 135 can be or include any suitable type of user interface device configured to enable user interaction between a user and expression mapping platform 130. For example, user interface 135 can be configured to provide (e.g., display) output (e.g., from mapping application 132 and/or from sampling profiler 133). Further, user interface 135 can be configured to receive user input (e.g., from a user at expression mapping platform 130), as described herein, via for example, one or more input and/or output devices including: a keyboard, a mouse, displays, screens/touchscreens, projectors, and the like (i.e., user interface 135 can be configured to implement any suitable type of humanmachine interface device, human-computer interface device, a batch interface, graphical user interface (GUI), and the like). User interface 135 can otherwise include or be configured to implement any suitable type of interface (e.g., user interface 113).

Communicator 137 can be or include, for example, a hardware device operatively coupled to processor 131 and memory 139, and/or software stored in memory 139 and executable by processor 131, capable of enabling and supporting communications over a network (e.g., network 102) and/or directly between or among compute devices (e.g., user device 110 and expression mapping platform 130). For example, communicator 137 can be or include a network interface card (NIC), a network adapter such as a Transmission Control Protocol (TCP)/Internet Protocol (IP) adapter card or wireless communication adapter (e.g., a 4G wireless communication adapter using Orthogonal Frequency Division Multiple Access (OFDMA) technology), a Wi-Fi™ device or module, a Bluetooth® device or module, and/or any other suitable wired and/or wireless communication device. Communicator 137 can be configured to connect or interconnect expression mapping platform 130 and one or more other devices (e.g., user device 110) for data communications therebetween, such as over a communications network (e.g., network 102). Communicator 137 can be configured to be implemented in conjunction with any suitable architecture, such as one designed for passing data and/or control information between processors (e.g., processor 111, processor 131), system memory (e.g., memory 117, memory 139), peripheral devices (e.g., user interface 113, user interface 135), and any other devices or components (e.g., of expression mapping system 100 and/or including expression mapping platform 130) within a system such as an expression mapping system (e.g., expression mapping system 100), as described herein.

Memory 139 can be or include any suitable type of memory, data storage, or machine-, computer-, or processor-readable media capable of storing a machine or computer program, digital information, electronic information, and the like (e.g., of or associated with mapping application 132). For example, memory 139 can be configured to store an application or program such as mapping application 132, such as for execution by processor 131. Memory 139 can be or include a memory buffer, a hard drive, a magnetic disk storage device of an internal hard drive, magnetic tape, magnetic disk, optical disk, portable memory (e.g., flash drive, flash memory, portable hard disk, memory stick), a semiconductor storage device such as a random access memory (RAM) (e.g., RAM including cache memory), a read-only memory (ROM), an erasable programmable read-only memory (EPROM), an electrically erasable programmable read-only memory (EEPROM), and/or the like. Memory 139 can otherwise include any suitable type of memory or data storage, as such may be chosen as a matter of design.

User interface 113 and/or user interface 135 can include, for example, a user interface display in which one or more displays are provided. The user interaction can include, for example, interactive association (e.g., based on user input) of one or more of a tissue image, a visualization, a user-selectable dataset, and one or more of a plurality of scanning records. In some embodiments, the one or more displays can be configured to be interconnected, and can include, for example, a first display, a second display, a third display, and/or a fourth display. For example, in some embodiments, the unified user interface can be configured to effectively operate, via and/or in conjunction with the first display, the second display, the third display, and/or the fourth display, as sections/portions of a single display. For example, the unified the user interface can be configured to interactively associate, based on user input (e.g., to user interface 135), one or more of tissue images, the visualizations, the user-selectable datasets, and one or more of the plurality of scanning records. Such as described in further detail herein with reference to FIG. 5.

Expression mapping platform 130, in some embodiments, can be configured to analyze the biological matter based on user input (e.g., received at user interface 113 and/or user interface 135), such that after hybridization of probes to slide-mounted tissue sections, the oligonucleotide tags can be released from discrete regions of the tissue via UV exposure (e.g., at sample profiler 133), the released tags can be quantitated (e.g., at sample profiler 133 and via the digital analyzer) in an nCounter assay (for example), and counts can be mapped back to tissue location, yielding a spatially-resolved digital profile of analyte abundance. The spatially-resolved digital profile can be configured to be displayed, for example, at user interface 113 and/or user interface 135, as described herein.

In some embodiments, ROIs are identified on/adjacent a serial section of tissue so as to be provided with probes. In the first instance, in some embodiments, full "macroscopic-features" imaging methodology to cell/tissues of interest is performed, e.g., DAPI staining, membrane staining, mitochondrial staining, specific epitope staining, and specific transcript staining, to determine overall macroscopic features of cell/tissue of interest. Alternately, ROIs are identified on a serial section adjacent to the serial section to be provided the probes; here, full "macroscopic-features" imaging (as described above) is performed on a first serial section. This imaging will generally identify ROIs on the adjacent serial section where signal oligonucleotides will be released from the probes upon application of a suitable and directed force. Serial sections may be approximately 5μπι to 15μπι from each other. Further details can be found in related PCT application no. PCT/US2016/042455, which is incorporated herein by reference in its entirety, as noted above.

In this example, expression mapping platform 130 can be configured to analyze (e.g., at sample profiler 133) the biological matter as follows:
Process: FFPE slide mounted tissue is incubated with a cocktail of primary antibodies conjugated to DNA oligos via a photo-cleavable linker, together with a limited number of visible-wavelength imaging reagents;
View: ROIs are identified with visible-light based imaging reagents at low-plex to establish overall "architecture" of tumor slice (e.g., image nuclei and/or using one or two key tumor biomarkers);

Profile: Select ROIs are chosen for high-resolution multiplex profiling and oligos from the selected region are released following exposure to UV light;

Plating: Free photocleaved oligos are then collected, e.g., via a microcapillary-based "sipper", and stored in a microplate well for subsequent quantitation; and/or Digitally Count: During the digital counting step, photocleaved oligos from the spatially resolved ROIs in the microplate are hybridized to 4-color, 6-spot optical barcodes, enabling up to ~1 million digital counts of the protein targets (distributed over up to 800-plex markers) in a single ROI using standard NanoString nCounter read-out instrument (e.g., SPRINT, Flex, and MAX).

Images may be processed internally, with each lane producing (in some embodiments) one RCC (Reporter Code Count) file containing the counts for that lane. Such RCC files can be compressed (e.g, "zipped") and downloaded for importation into mapping application 132 (e.g., nSolver™ software) analysis (and optionally quality control). Run data can then be exported, for example, as a comma separated values (CSV) format file that can be opened by most commonly used spreadsheet packages (e.g., Microsoft® Excel), and can be analyzed using analysis software (e.g., NanoString's nSolver or other data analysis and visualization software packages).

Figure 2:
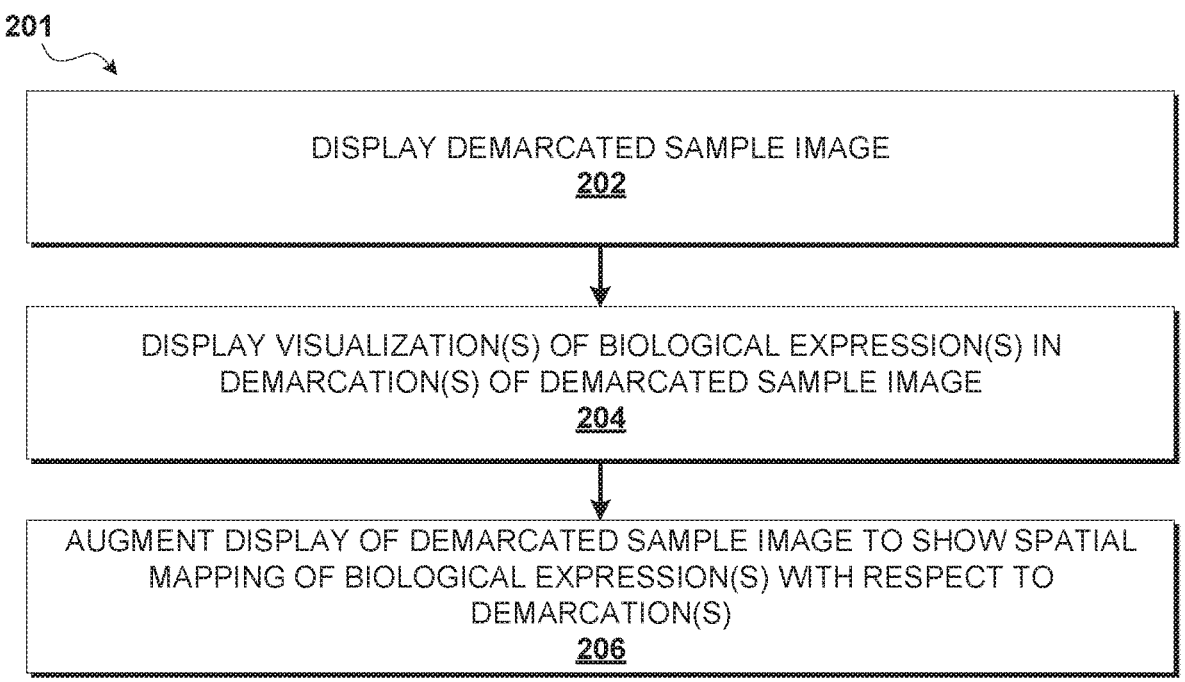
FIG. 2 is a flowchart depicting an example of a method of operating an expression mapping system, in accordance with some embodiments of the present disclosure.

FIG. 2 is a flowchart depicting an example of a method of operating an expression mapping system ("method 201"), in accordance with some embodiments. Method 201 can be implemented, for example, via an expression mapping system such as expression mapping system 100 (e.g., see FIG. 1 and associated description). Accordingly, method 201 can be implemented to show spatial mapping of biological expressions within one or more ROIs of a tissue sample; specifically, in some embodiments, spatial mapping can be configured to show, for example, a spatially-resolved analyte profile in and of the tissue sample (e.g., within the ROIs), corresponding to occurrences and measurements of expression events in the tissue sample, as described herein.

The method 201 includes, at 202, causing the expression mapping system to display, in a first display, a scans pane which can include, for example, at least the image of the tissue sample, the image including one or more demarcations each corresponding to a particular one of one or more regions-of-interest (ROIs), and each of the one or more ROIs corresponding to a specific portion of the tissue within the tissue image. The scans pane is described, for example, in further detail herein with reference to FIG. 5. The method 201 includes, at 204, causing the expression mapping system to display, in a second display, a visualization pane that includes, for example, a visualization of each of the respective biological expressions contained in the one or more ROIs. Such visualizations are described, for example, in further detail herein with reference to FIG. 5.

The method 201 includes, at 206, causing the expression mapping system to augment the first display by coding the one or more ROIs in the tissue image to show the spatial mapping of the biological expressions within the one or more ROIs. In some embodiments, the expression mapping system can be configured to augment the first display to facilitate morphological profiling (e.g., of tissue) in at least one of the one or more ROIs, such as described with reference to FIGS. 4A-E. For example, in some embodiments, the coding can include, for example, color-coding, such as described with reference to FIGS. 4A-E. In some embodiments, one or more of the coding or the color-coding can include, for example, presenting a quantitative measurement of the biological expressions, respectively, such as described with reference to FIGS. 3, 4A-E, and/or 6A-I.

In some embodiments, the first display can be augmented based upon user input specifying at least one selection of a biological expression contained in the visualization. In some embodiments, the spatial mapping of the at least one user selected biological expression can be configured to provide spatial context thereof to at least one of the one or more of the ROIs, such as described herein with reference to FIG. 5. In some embodiments, the user input specifying the selection of the one or more ROIs can include, for example, a selection of one or more of the ROIs defining, for example, a shape or size of the one or more ROIs associated with the selection.

In some embodiments, the method 201 can further include, for example, displaying, in a third display, a datasets pane which includes at least one user-selectable dataset, the at least one dataset associated with one or more of the biological expressions contained in the one or more ROIs, such as described with reference to FIG. 5. In some embodiments, the method 201 can further include, for example, displaying, in a fourth display, a records pane which includes a plurality of scanning records, each containing at least one tissue image. In some embodiments, the method 201 can further include, for example, selecting, based on the user input, at least one record, such that, upon selection thereof, at least one of the scans pane, the visualization pane, and the datasets pane is displayed in a respective or associated display.

Figure 3:
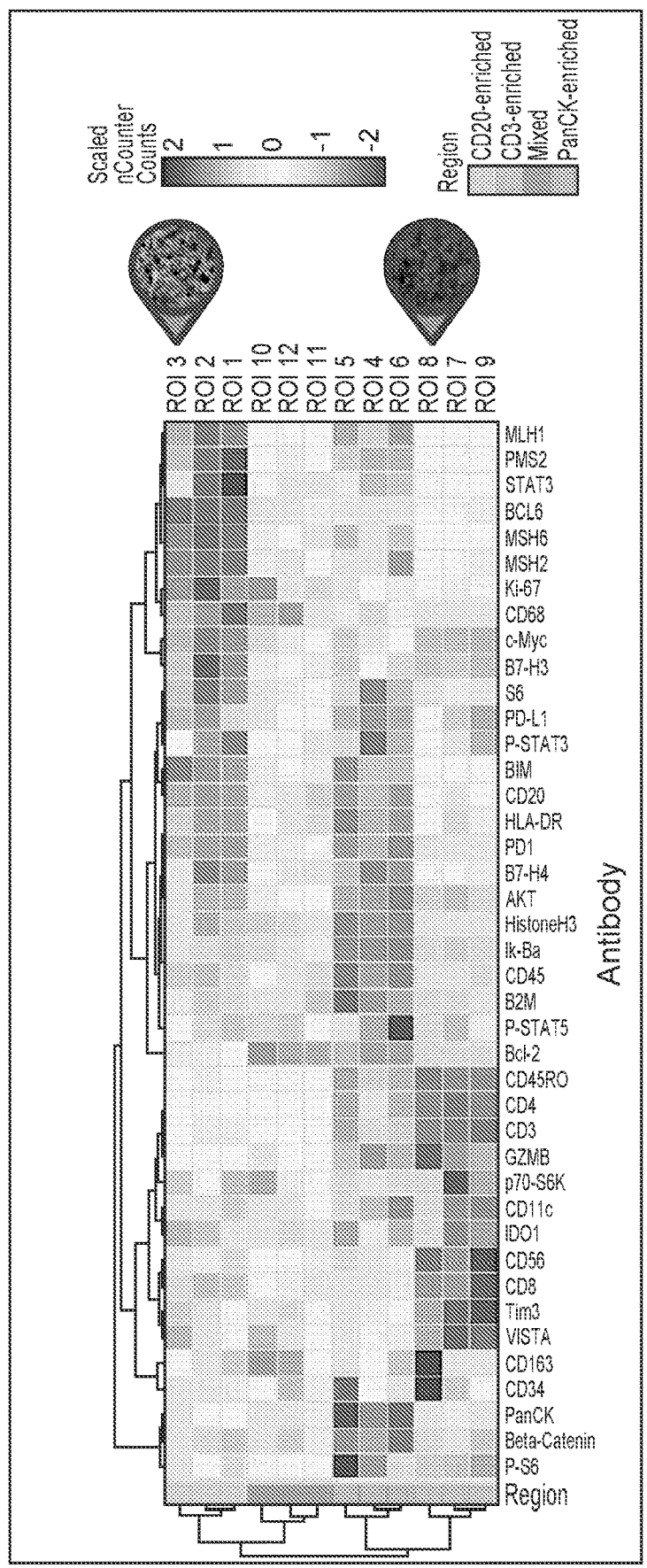
FIG. 3 is an illustration depicting an example of a visualization showing gene expression, in accordance with some embodiments of the present disclosure.

FIG. 3 is an illustration depicting an example of a visualization showing gene expression, in accordance with some embodiments. As shown, the visualization can include, for example, a map such as a heat-map, and the like, in which regions (e.g., ROIs) of a sample have been classified based on the intensity and identity of the markers expressed. Further, (from top to bottom), exemplary ROIs include "ROI 3", ""ROI 2", "ROI 1", "ROI 10", "ROI 12", "ROI 11", "ROI 5", "ROI 4", "ROI 6", "ROI 8", "ROI 7", and "ROI 9". Moreover, (from top to bottom), exemplary regions include "CD20-enriched", "CD3-enriched", "Mixed", and "PanCK-enriched". Moreover, exemplary antibodies, as shown (from left to right), include "P-S6", "Beta-Catenin", "PanCK", "CD34", "CD163", "VISTA", "Tim3", "CD8", "CD56", "IDO1", "CD11c", "p70-S6K", "GZMB", "CD3", "CD4", "CD45RO", "Bcl-2", "P-STAT5", "B2M", "CD45", "Ik-Ba", "HistoneH3", "AKT", "B7-H4", "PD1", "HLA-DR", "CD20", "BIM", "P-STAT3", "PD-L1", "S6", "B7-H3", "c-Myc", "CD68", "Ki-67", "MSH2", "MSH6", "BCL6", "STAT3", "BCL6", "STAT3", "PMS2", and "MLH1". Further, the heat-map can include, for example, one or more legends configured to indicate type and degree of respective biological expressions. For example, as shown, the heat heat-map can include a "scaled nCounter Counts" legend and a "Region" legend.

The heat-map represents a visualization of data (e.g., from sample profiler 133) showing color-coded, quantitative measures or counts of various biological expressions with respect to associated ROIs with which the biological expressions, or expression events associated with the biological expressions, are mapped. The heat-map can be or include an image that depicts counts by color, which can include segments configured to be aligned along the x-axis and targets on the y-axis. The heat-map can be displayed via color-coding of the one or more ROIs so as to present the heat-map such that it presents a quantitative measurement of the biological expressions. For example, the counts by color of the heat-map can be configured to show quantitative measurements such as counts of biological expressions (e.g., indicated by "scaled nCounter Counts" legend) with respect to regions of the sample to which the counts of biological expressions are mapped (e.g., indicated by "Region" legend). Moreover, the quantitative measurement can be configured to correspond to a type (e.g., via Region and/or ROI and associated antibody type) and/or degree (e.g., via counts) of the respective biological expressions. Moreover, the heat-map can be configured to show the degree or extent of each respective biological expression via corresponding color or intensity. For example, as shown in the heat-map, higher intensity (e.g., relatively darker regions) can be configured to indicate higher biological expression counts, and lower intensity (e.g., relatively lighter regions) can be configured to indicate lower biological expression counts.

In some embodiments, the heat-map can be configured to display an interactive pop-up box that can be shown in response to user input corresponding to hovering (e.g., a cursor) over an area of the heat-map. In some embodiments, the interactive pop-up can be configured to show, for example, a segment, target, count, and/or any tags associated with the area over which the hovering is detected. In some embodiments, a user input element corresponding to a scroll or slide can be shown and configured to enable selections between Linear and Log 2 data. In some embodiments, a color-scheme by which the heat-map is displayed can be configured to be adjusted or changed based on user input. As an example, the heat-map can be configured for interactive user-manipulation, for example, as follows: click and drag to select part or all of the heat-map; select, define, and/or specify a probe group comprised of selected probes; unselect, undefine, and/or unspecify a probe group (e.g., from a current study); and the like. In some embodiments, the heat-map can be implemented, for example, on a linear scale, a log scale, and the like.

Figure 4A:
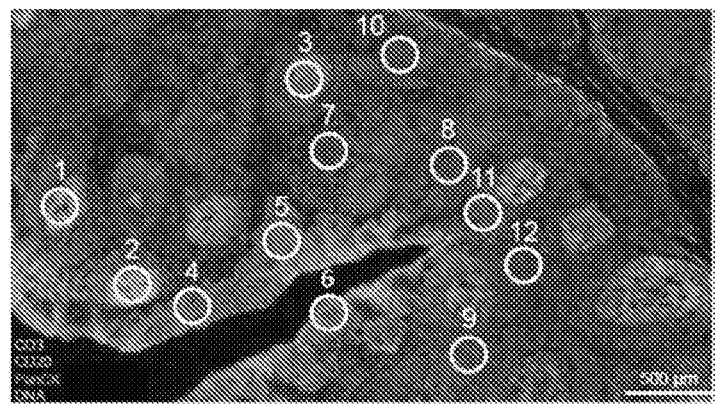
FIGS. 4A-E are illustrations depicting examples of visualization and profiling modalities by and in which tissue and gene expression can be shown, in accordance with some embodiments of the present disclosure.
Figure 4B:
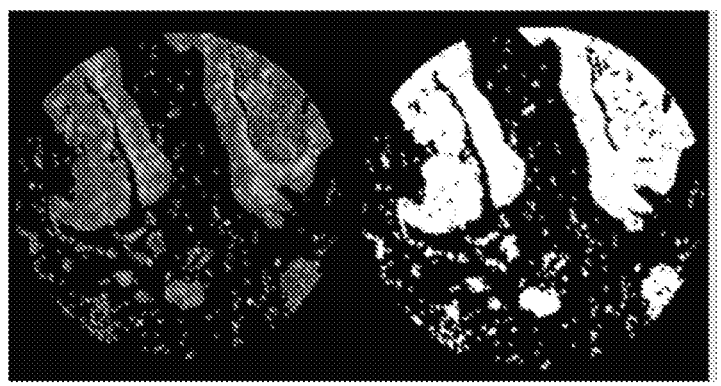
Figure 4C:
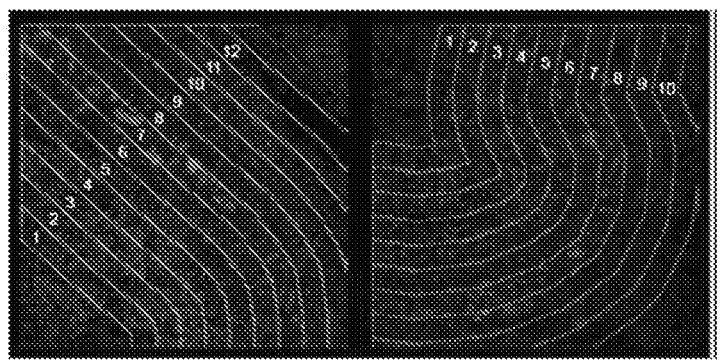
Figure 4D:
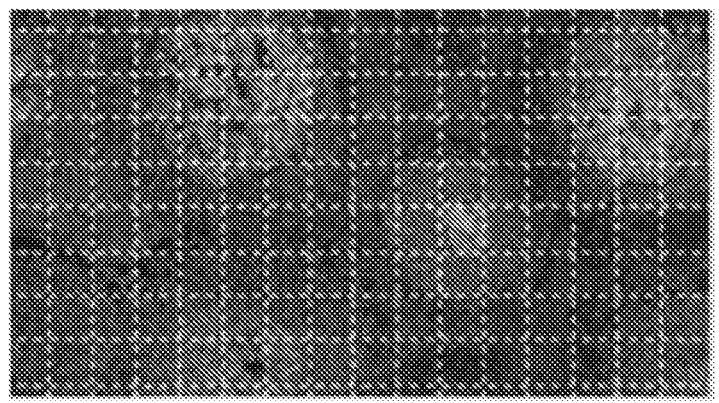
Figure 4E:
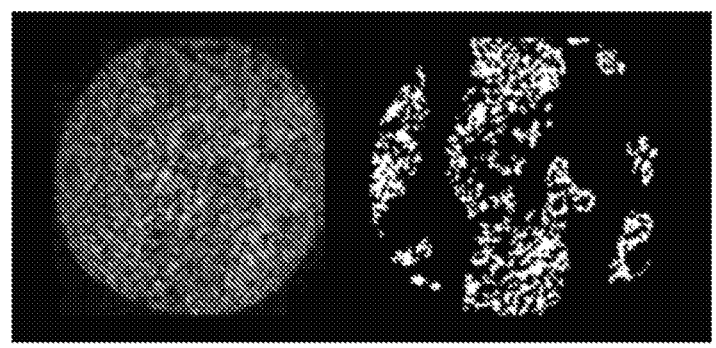

FIGS. 4A-E are illustrations depicting examples of visualization and profiling modalities ("visualization and profiling modalit(ies)" or "profiling modalit(ies)") by and in which tissue (e.g., tissue sample) and gene expression (e.g., occurrences of expression events across or within the tissue) can be shown (e.g., via user interface 113 and/or user interface 135), in accordance with some embodiments. As shown, the visualization and profiling modalities include geometric profiling (FIG. 4A), segment profiling (FIG. 4B), contour profiling (FIG. 4C), gridded profiling (FIG. 4D), and rare cell profiling (FIG. 4E). The visualization and profiling modalities can be configured to enable a user to interactively and visually define, based on user input, one or more ROIs, as described herein. The visualizations and profiling modalities can be generated and configured so as to facilitate morphological profiling (e.g., of tissue) in at least one of the one or more ROIs, as described herein. For example, the visualizations and profiling modalities can be configured for analysis of a sample to determine, assess, and/or characterize a level of heterogeneity of expression events and associated biological expressions in and of the sample.

Referring now to FIG. 4A, geometric profiling can be configured to enable, support, and facilitate spatial and quantitative assessment, evaluation, and characterization of sample heterogeneity and/or profile (e.g., biological expression profile) based on user input. In some embodiments, the user input can be configured to specify, adjust, and/or define one or more selections of one or more ROIs in terms of shape and/or size. For example, the user input specifying the selection of the one or more ROIs can include, for example, a selection of one or more of the ROIs along with a shape or size of the one or more ROIs associated with the selection of the one or more ROIs. The same shape can be reused, ensuring that the specific area (in pixels) is the same between ROIs. In some embodiments, the geometric profiling can be configured to provide for standardized geometric shapes across distinct tissue regions of the sample. As an example, the geometric profiling can be configured to facilitate assessment of how expressions of tumor and immune markers may differ across a sample (e.g., heterogeneity). The geometric profiling can be configured for identification of distinct expression profiles across and within specific regions of the tissue expression profiles based on proximity. In some embodiments, the geometric profiling can be configured to represent a quantification of biological expression within a chosen one or more ROIs.

Referring now to FIG. 4B, segment profiling can be configured to show a type and/or degree of cellularity using morphology markers to identify and profile distinct biological compartments within one or more ROIs. Segment profiling reveals unique tumor and tumor microenvironment molecular profiles. For example, the segment profiling can be configured to facilitate assessment of how a tumor may differ from the tumor microenvironment. In some embodiments, the segment profiling can include, for example, manual segment profiling or automatic segment profiling. In some embodiments, the automatic segment profiling can be configured to automate and facilitate segment profiling of a sample in at least one of the one or more ROIs based on user input specifying at least one segment profiling parameter. In some embodiments, the segment profiling can be configured to detect, classify, identify, and/or distinguish or otherwise determine differences between high and low signals (e.g., in terms of type and/or degree) from morphology markers (fluorescent targets) to facilitate identification and profiling of distinct biological areas within one or more ROIs, as described herein. For example, the segment profiling can be configured to identify and/or profile distinct biological areas within an ROI to distinguish between distinct biological areas such as CD45-positive versus S100B-positive tissue.

Referring now to FIG. 4C, contour profiling can be configured to enable, support, and facilitate assessment, evaluation, and characterization of the effect of proximity on biological response and the local microenvironment around a central structure in one or more ROIs, as described herein. For example, the contour profiling can be configured to determine how proximity to a tumor or an immune cell population alter biological response (e.g., in one or more ROIs). In some embodiments, the one or more ROIs can include one or more radiating ROIs configured to show distinct expression profiles based on proximity, such as shown in FIG. 4C. In some embodiments, the contour profiling can be configured to show how proximity affects biological response by examining the local microenvironment around a central structure using radiating ROI. Central structures can be compact, such as clusters of immune cells, or complex, like a neuron or blood vessel. Accordingly, the contour profiling can be configured to enable, support, and facilitate assessment, evaluation, and characterization of the effect of proximity on biological response and the local microenvironment around a central structure in one or more ROIs, where the central structure includes, for example, compact, clusters of immune cells, or complex, like a neuron or blood vessel.

Referring now to FIG. 4D, gridded profiling can be configured to perform deep spatial mapping using a tunable gridding pattern. For example, the gridded profiling can be configured to provide a digital map of the molecular profile of a structure (e.g., a tumor) in a sample, based on user input corresponding to a selection of one or more ROIs, as described herein. In some embodiments, a visualization of the gridded profiling can include, for example, a tunable gridding pattern that is overlaid on the image to drive deep spatial mapping of a sample.

Referring now to FIG. 4E, rare cell profiling can include, for example, single cell profiling and rare cell profiling. Isolated immune cell populations show unique expression profiles. Accordingly, the rare cell profiling can be configured to show, for example, the function of distinct cell populations within one or more ROIs, as described herein. In some embodiments, the rare cell profiling can be configured to detect or identify distinct cell populations based on cell type specific morphology markers in one or more ROIs. Accordingly, the rare cell profiling helps "shine a light on rare events," including, for example, rare expression events and types thereof, as may be associated with corresponding biological expressions. In some embodiments, the rare cell profiling can be configured to facilitate assessment, evaluation, and characterization of how particular immune cells, including, for example, rare or single immune cells can impact tumor biology and therapeutic response. The function of the distinct cell populations can be shown, for example, based on cell type-specific morphology markers corresponding to the unique expression profiles.

Figure 5:
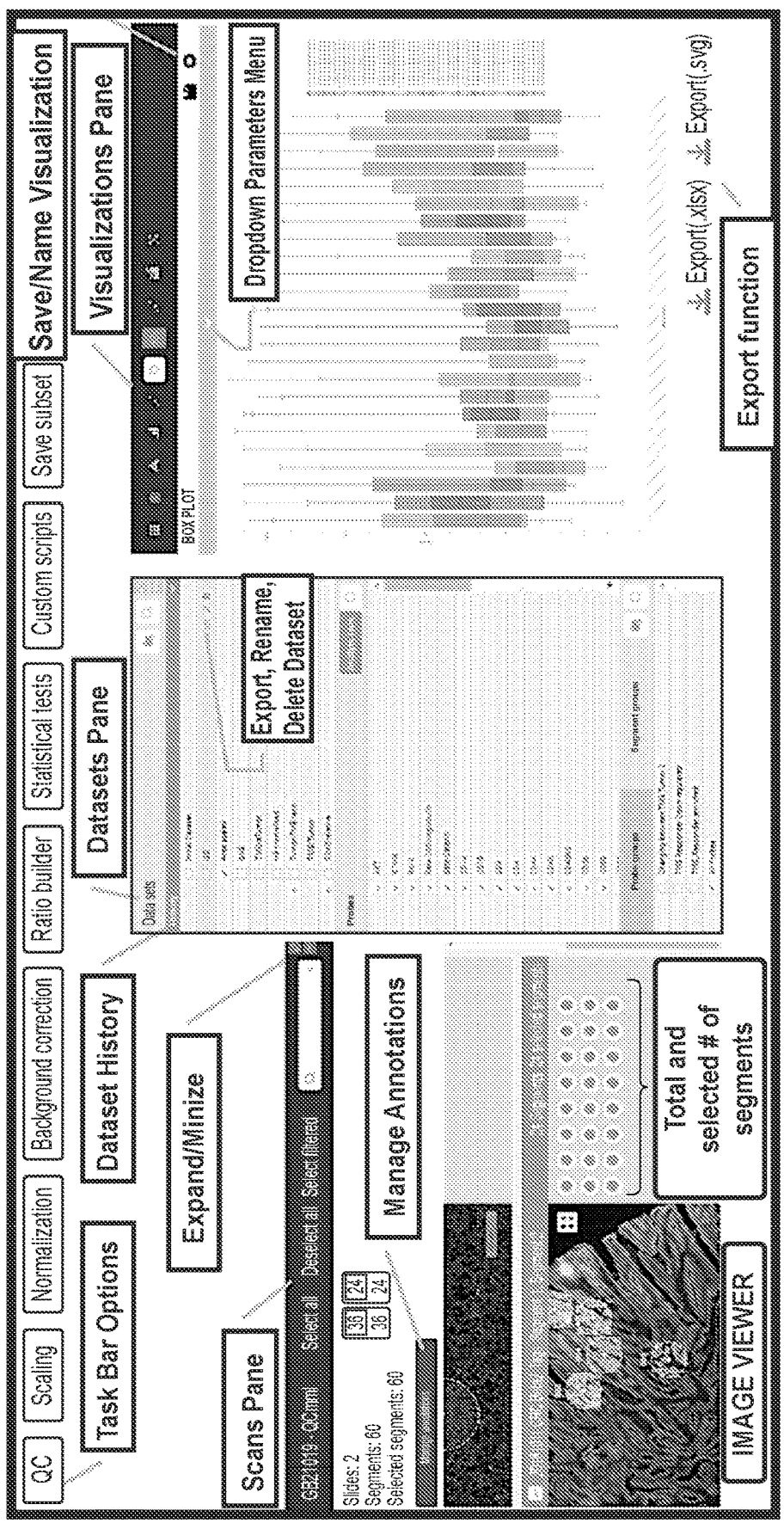
FIG. 5 is an illustration depicting an example of a user interface display that includes interconnected visualizations, in accordance with some embodiments of the present disclosure.

FIG. 5 is an illustration depicting an example of a user interface display that includes visualizations, in accordance with some embodiments. The user interface display can include a user interface such as user interface 113 and/or user interface 135, as described herein (and above). As shown, the user interface display include, for example, a scans pane, a datasets pane, and a visualizations pane. In some embodiments, the user interface display can further include, for example, a records pane (not shown). Further, the scans pane, the datasets pane, and the visualizations pane can respectively include various function buttons. For example, the function buttons can include, in the scans pane, "Manage Annotations"; in the Datasets Pane, "Dataset History" and "Export, Rename, Delete Dataset", and in the Visualizations Pane, "Dropdown Parameters Menu", as shown in FIG. 5. In some embodiments, the user interface display can further include, for example, a toolbar and/or general function buttons. For example, as shown, the toolbar can include "Task Bar Options", and the general function buttons can include "Export Function". The user interface display can otherwise include any other suitable type or configuration of panes, toolbars, and/or function buttons, as such may be chosen as a matter of design.

The user interface display can include a unified user interface configured to provide for interactive user interaction between a user (e.g., at user device 110 or expression mapping platform 130) and an expression mapping platform (e.g., expression mapping platform 130), as described herein. In some embodiments, the user interaction can include, for example, interactive association (e.g., based on user input) of one or more of a tissue image, a visualization, a user-selectable dataset, and one or more of a plurality of scanning records. In general, the interconnected visualizations can include any suitable type of visualization and/or image(s) (e.g., of a sample) associated, for example, with a selection of a dataset (e.g., one or more user-selectable datasets; one or more of a plurality of scanning records, as described herein.

In some embodiments, the scans pane can include, for example, a plurality of icons each corresponding to a specific segment within at least one of the one or more ROIs or the overall tissue image. In some embodiments, the scans pane can include, for example, a plurality of icons each corresponding to a specific segment within at least one of the one or more ROIs or the overall tissue image. In some embodiments, the scans pane can include, for example, representations, visualizations, and/or images associated with or corresponding to scans, one or more ROIs, segments, and the like. In some embodiments, the scans pane can be configured such that one or more of the scans, the one or more ROIs, and/or one or more of the segments can be excluded or included in a particular study (e.g., such as shown in FIG. 5) based on and responsive to user input (e.g., received from a user at user device 110 and/or expression mapping system 130 via user interface 113 and/or user interface 135) corresponding to a selection of one or more of the scans, the one or more ROIs, and/or one or more of the segments. Moreover, the scans pane can be configured to provide for user-input based selection of tags. Further, the scans pane can include individual image viewers of the scans.

For example, the scans pane can include, for example, an icon associated with each scan (e.g., located at the top of this pane and picker buttons representing each segment are located to the right of each image viewer, as shown in FIG. 5). In some embodiments, each icon can be interactively associated with each scan such that, for example, a single click will switch the state of a scan or segment from selected to unselected and vice-versa. The icons can otherwise be configured to provide for other control operations, as such may be chosen as a matter of design. In some embodiments, the scans pane can be configured such that hovering over an icon or picker button displays additional information such as name, tags, etc.

In some embodiments, the scans pane can include, for example, a SCAN ICONS button, configured to provide a visual preview of: a number of segments selected and/or a total number of segments for analysis; and a general proportion of segments selected for analysis. In some embodiments, the scans pane can include, for example, an image viewer. Each image viewer portrays the scan and the spatial placement of the ROIs and segments. For example, the checkbox in the upper left corner indicates whether that scan is selected for analysis, as shown in FIG. 5. Selected scans have a green header. Deselected scans have a white header. The scans pane can be configured to adjust the scan image to assist in viewing, selecting, and deselecting segments. For example, the scan image be adjusted to change a field of view of a segment. As another example, the scan image can be configured to be zoomed in and out (e.g., via user interface 113 and/or user interface 135). In some embodiments, the scans pane can include one or more picker buttons, each corresponding to one or more ROIs (e.g., scan image).

In some embodiments, the datasets pane can include, for example, representations, visualizations, and/or images associated with or corresponding to one or more datasets, probes, probe groups, and/or segment groups. For example, the datasets pane can include a list that includes the representations, visualizations, and/or images. In some embodiments, the datasets pane can be configured to initially show the datasets and probe groups associated with a current study. For example, the datasets pane can be configured to show an initial dataset (the raw set of imported data; this will appear at the top of the Dataset list) and the All Probes group at the onset of a new study.

In some embodiments, the visualizations pane can include, for example, one or more visualizations, each respectively corresponding to one or more of a graph, plot, diagram, and map of one or more biological expressions contained in one or more ROIs, as described herein. Each visualization can include a visual representation of one or more selected datasets, probes, and/or adjustments applied to the data from those probes. In some embodiments, one or more of the visualizations can include one or more images (e.g., sample images). In some embodiments, one or more of the visualizations can be configured such that user input corresponding to a selection of an area of interest (e.g., ROI) on a plot causes the relevant highlighted segments in the Scans pane to be shown. The selection of the area of interest can include, for example, right-click to create tags, groups, etc. For example, the visualizations pane can be configured such that an area of interest in any visualization can be selected (e.g., by a user based on user input to user device 110 and/or expression mapping platform 130 via user interface 113 and/or user interface 135) to show the respective segments highlighted in the Scans pane. In some embodiments, one or more ROIs can be selected via the visualizations pane. In some embodiments, the visualizations pane can be configured for real-time user-interaction via user input corresponding to selections of changes that can be applied to, for example, make data adjustments in real time.

In some embodiments, the visualizations pane can be configured to generate, based on user input, a probe group, a segment group, and/or the like. In some embodiments, the visualizations pane can be configured to generate, based on user input, a tag for association with one or more selections of one or more sets of segments, and/or discrete, individual segments. In some embodiments, the visualizations pane can be configured to dynamically display, in response to user input, one or more datasets, segments, and/or probes. In some embodiments, the visualizations pane can be interactively interconnected to one or more of the scans pane or the datasets pane. For example, the visualizations pane can include a visualization configured such that one or more ROIs can be selected via selection of an area of interest of the visualization. In some embodiments, a selected ROI in the visualizations pane can be configured to be shown, highlighted, or otherwise indicated in the Scans pane. Accordingly, the visualizations pane can be configured to enable a user to generate a probe group or segment group for the selection, to exclude selected set of probes or segments from a study, to define tags for association with one or more selected segments, and the like. In some embodiments, the records pane and/or the datasets pane can be configured to indicate any changes or adjustments that are made to associated datasets.

As an example, in use, the datasets pane can include a list of all datasets and probe groups associated with a current study. In some embodiments, the datasets pane can be configured to show an initial dataset at the onset of a study. For example, the initial dataset can include a raw set of imported data; which can be configured to be shown at the top of the Dataset list) in the Data sets field. As another example, the initial dataset can be configured to include a probes group, as well as any additional probe groups defined in your core and module kit configuration files that populates the Probe groups field at the onset of a study.

In some embodiments, the user interface display can be configured to render, for display via the unified user interface and in real-time based on user input, the scans pane in conjunction with the visualization pane and one or more of the datasets pane and the records pane. In some embodiments, detected probes of a dataset can be listed in a probe list in the Datasets pane. The datasets pane can be configured such that individual datasets can be saved (e.g., via drag and drop operation) into the records pane. In some embodiments, the records pane can include, for example, a folder or list of datasets (e.g., saved datasets). In some embodiments, the records pane can be configured to be searchable based on tag, text, and the like. In some embodiments, the user interface display can be configured to select, based on user input, at least one record, such that, upon selection thereof, at least one of the scans pane, the visualization pane, and the datasets pane is displayed in a respective display, such as shown in FIG. 5.

In some embodiments, the records pane can include a data analysis queue. For example, the records pane can be configured to be accessed via a records button, and to enable user-input based selection of one or more folders containing one or more scans. Select each scan of interest by clicking the checkbox in the upper-left corner. This will turn the header a color, for example (e.g., green). One slide at a time may be viewed as well. In some embodiments, the records pane can include a Scan Gallery View (e.g., under Records as shown in FIG. 5). In some embodiments, the records pane be configured such that one or more scan(s) can be queued together for an analysis based on user input. In some embodiments, the records pane can be configured to adjust, based on user input, a scan order. For example, the scan order can be automatically set based on scan date. As another example, the scan order can be adjusted, based on user input, with respect to Scan Name, Slide Name, and the like.

In some embodiments, the user interface display can be configured to filter, based on user input, at least one of a property, constraint, and/or value for the plurality of records. For example, the user interface display can be configured to filter probes based on Analyte Type (e.g., to enable a user to choose RNA or Protein to filter the probes that appear), based on text and/or tag (e.g., to search for probes by text and/or by tag). Probe groups and segment groups can be listed, for example, in the Datasets pane. Other predefined probe groups may auto-populate in this field as they are defined in the core or module kit configuration file. In some embodiments, the filtering can be configured to be implemented, for example, based on selections of Tags to allow grouping of segments by type and can then be used to categorize and filter data for analysis.

As an example, in use, the scans pane can be configured to enable a user to select, based on user input, one or more scans, probes, and/or segments to include in a study. One or more of the scans in the study can be represented, for example, as scan icons at the top of the scans pane and as scan images listed downward, such as shown in FIG. 5. In some embodiments, the scans pane can be configured such that substantially all scans and segments will be initially selected for analysis in the study. In some embodiments, the scans pane can be configured such that segment annotations can be uploaded to a spreadsheet using the Manage Annotations button in the Scans pane. In some embodiments, the scans pane can include FIGS. 6A-I are illustrations respectively depicting examples visualizations, in accordance with some embodiments. As shown, the visualizations include a cluster diagram (FIG. 6A), a bar chart (FIG. 6B), a scatter plot (FIG. 6C), a box plot (FIG. 6D), a forest plot (FIG. 6E), a statistical plot (FIG. 6F), a volcano plot (FIG. 6G), a trend plot (FIG. 6H), and a strip plot (FIG. 6I).

Figure 6A:
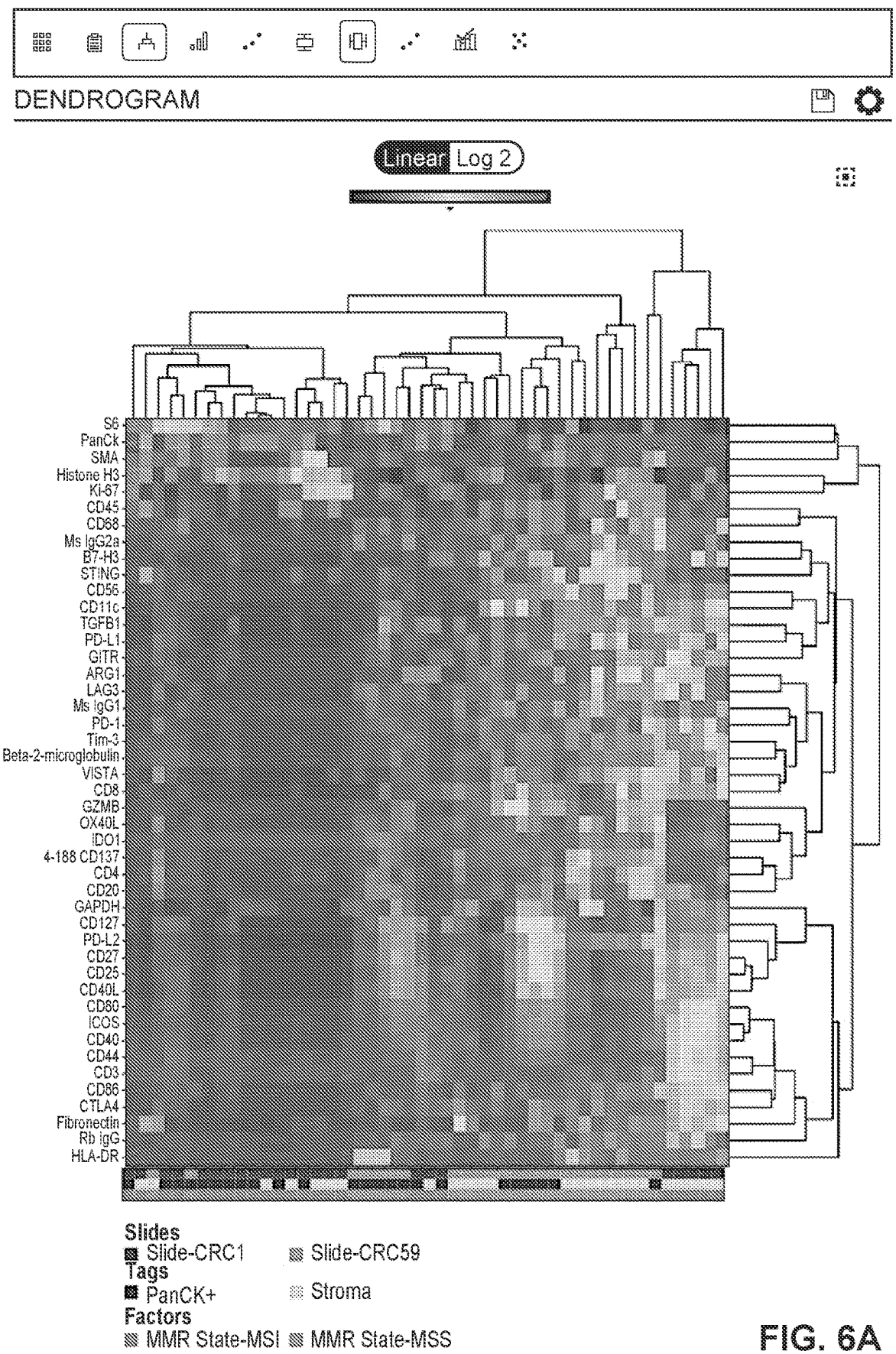
FIGS. 6A-I are illustrations respectively depicting examples visualizations, in accordance with some embodiments of the present disclosure.

With reference to FIG. 6A, the cluster diagram can include an interactive tree which makes inferences about relationships among data points. In some embodiments, the interactive tree can be or include a dendrogram. The cluster diagram can be configured to show points belonging to the same branch of a cluster are similar to each other at some level; data points in separate branches are less similar, where segments are aligned along the x-axis and targets on the y-axis, such as shown in FIG. 6A. In some embodiments, the cluster diagram can be implemented via an algorithm that is configured such that a selection, based on user input, causes data will be log transformed, then z-score will be calculated, Clustering (correlation/dendrogram will be calculated) to determine position in the cluster heat-map. The cluster heat-map will plot each segment-probe cell according to determined position in the color representing the z scores. Upon export of data from visualization, users should have ability to export values they see which is z-scores.

Figure 6B:
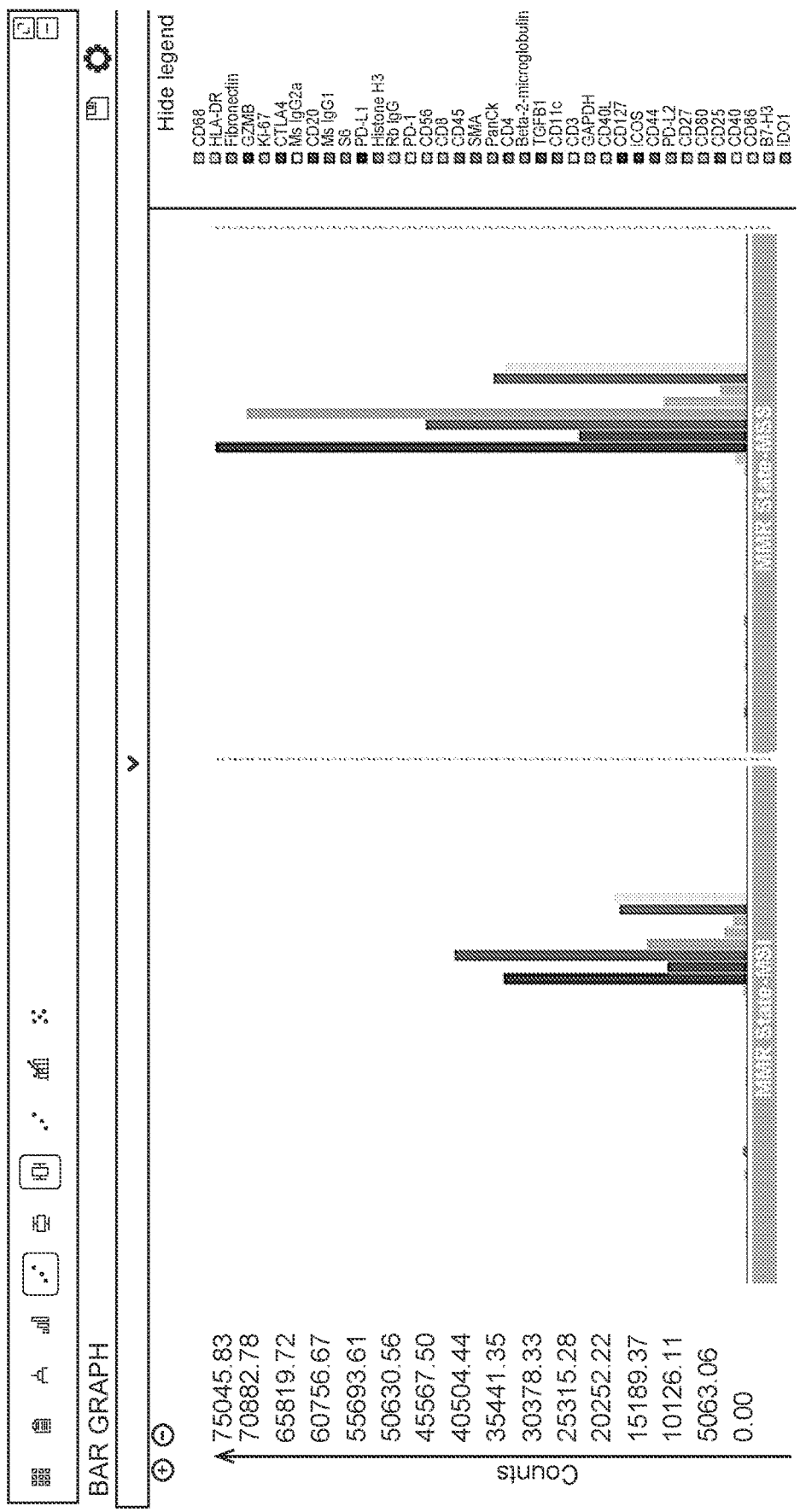

With reference to FIG. 6B, the bar chart represents the count values of all probes across all segments included in the study. For example, segments can be listed along the x-axis and counts along the y-axis; and the height of each bar represents the frequency of each count defined by the bins. In some embodiments, the bar chart can be implemented via an algorithm that is configured such that the bar chart is shown on a linear and/or log scale; and/or error bars are either the Standard deviation of count in a group, or standard error. In some embodiments, the bar chart can be configured such that intensity data can be autoscaled and/or viewed in linear or log space using the Linear/Log slider. In some embodiments, the bar chart can be configured to show ratio data (if applicable) as Ratios, Fold Changes, or Log 2 ratio. In some embodiments, the bar chart can be configured to apply, automatically or manually based on user input, scaling by entering a Min Count Value and/or a Max Count Value (only available when viewing linear intensity data, not in log scale). In some embodiments, the bar chart can be configured to provide for Apply grouping by selecting Tags, Factors, Average method (median, geomean, average), and Error bars (SE, SD, none).

Figure 6C:
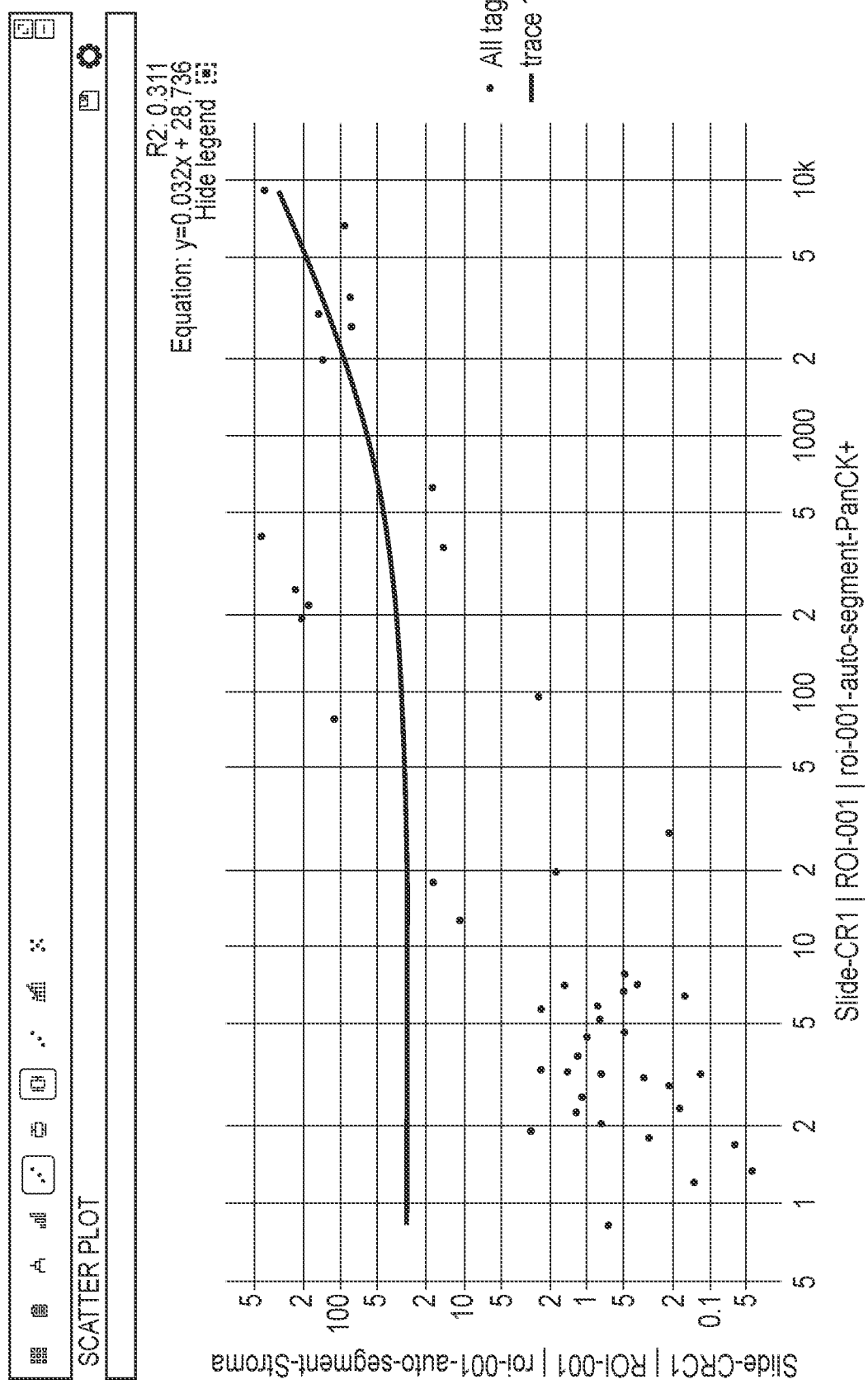

With reference to FIG. 6C, the scatter plot is a visualization that plots one segments' results on the x-axis and a different segments' results on the y-axis. Alternatively or in addition, the scatter plot can be or include a visualization configured to show a first plot showing a result associated with probes from a first study with respect to a second plot showing a result associated with probes from a second study. In some embodiments, the scatter plot can be configured to automatically show a trendline such as an R2 line and associated value (e.g., shown at upper right of the plot in FIG. 6C). In some embodiments, the R2 value can be configured to be calculated as the pearson correlation coefficient (e.g., 'RSQ" formula in Excel).

Figure 6D:
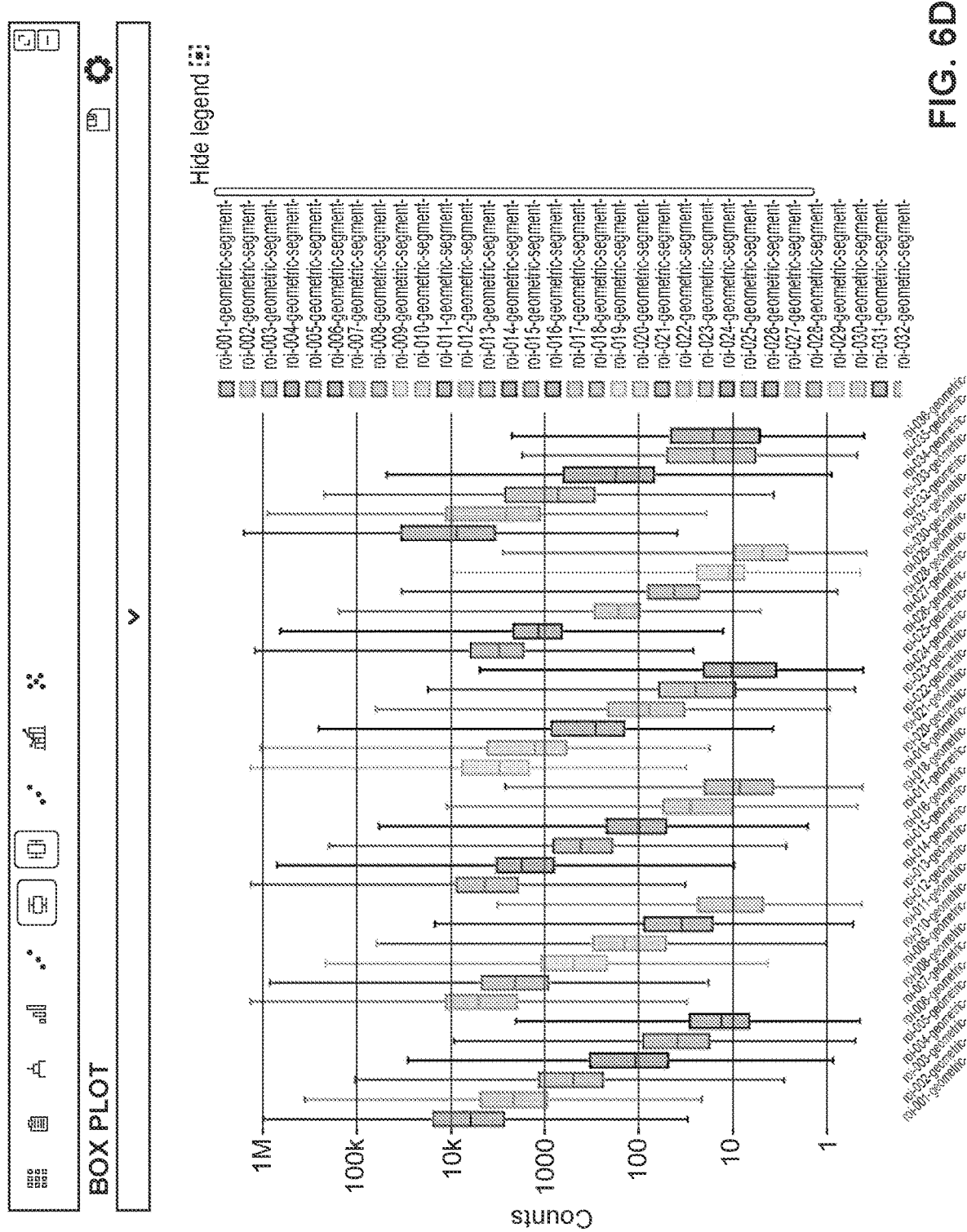

With reference to FIG. 6D, the box plot represents a plot depicting subsets of a study based on quartiles. Box plots have lines extending vertically from the boxes (whiskers) that indicate variability outside the upper and lower quartiles. Outliers may be plotted as individual points. These visualizations display differences between subsets of an experiment without making any assumptions about the underlying statistical distribution; they are non-parametric. For example, the box plot can be configured to show, based on user input, a popup displaying the segment, tags, and the values for the median, maximum, and first and third quartiles. The legend shows the color assigned to each plot and its corresponding label. Click a color box in the legend to either display or hide the plot. In some embodiments, the box plot can be configured so as to extend between 25th and 75th quartiles, and/or the whiskers extend to minimum and maximum.

Figure 6E:
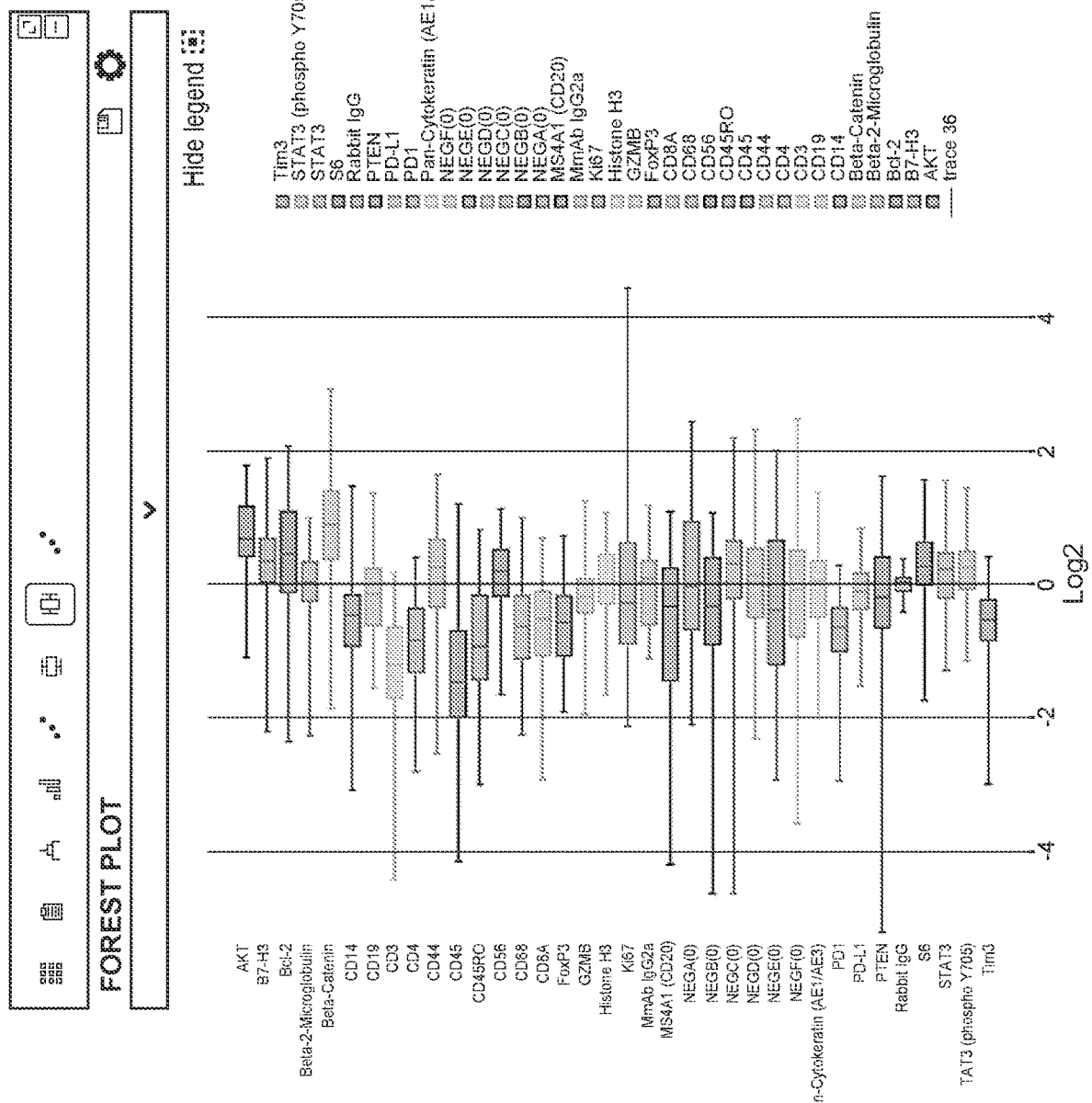

With reference to FIG. 6E, the forest plot shows the distribution of ratio values for individual probes across all segments or groups of segments. Fold changes are depicted as box and whisker plots along the horizontal axis against each probe name (listed vertically). A vertical axis is shown at ratio value equal to 1. Hover over a box to see a tooltip with the statistics for the distribution, depicted by the plot for each probe. The boxes span the first and third quartile of the distribution with a line indicating the median. Whiskers extend between the 95% confidence limits for the data. In some embodiments, the forest plot can include the following functions: view intensity data as Ratios, Fold changes, or in Log 2: Stratify and color data by grouping by tags and tag combinations; Color data points by tags; and/or Select one or more segment tag for coloring (combination groups will be created, as well).

Figure 6F:
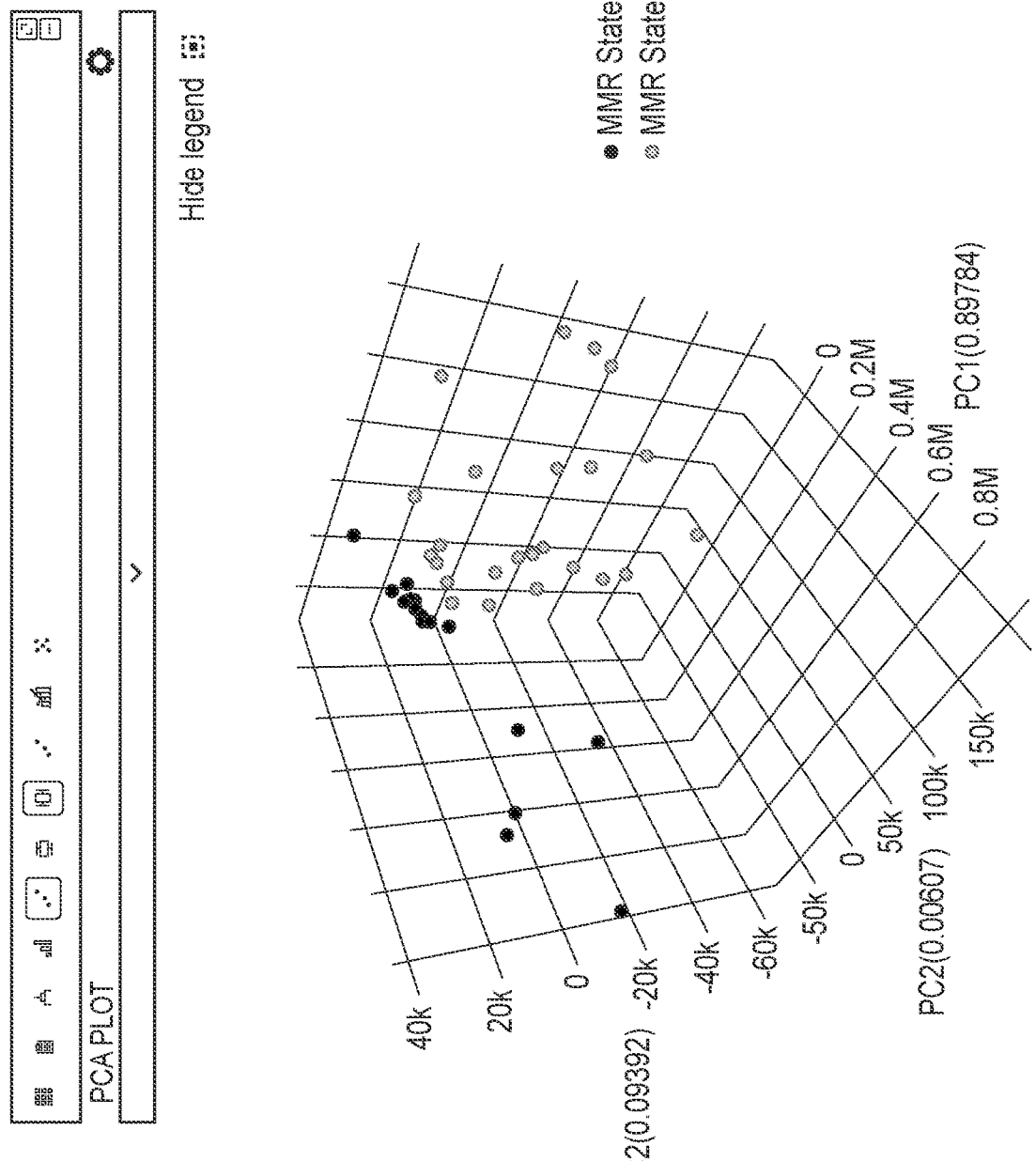

With reference to FIG. 6F, the statistical plot can include, for example, a principal component plot, or PCA plot. The principal component plot can be configured to depict the first three principal components for the selected dataset along the x-axis, y-axis, and z-axis of a three dimensional plot. The majority of sources of variation can be explained by these first three components. The principal component plot can be configured to include various functionality, as follows: click on the plot and rotate along the x, y or z axis to view the plot in different axes' perspectives; click on a data point to automatically highlight the segment in the segments pane and the scan image viewer; and/or hover over a datapoint on the plot to see a popup displaying the segment name it represents, associated tags, and each of its coordinates and to see its three dimensions defined.

Figure 6G:
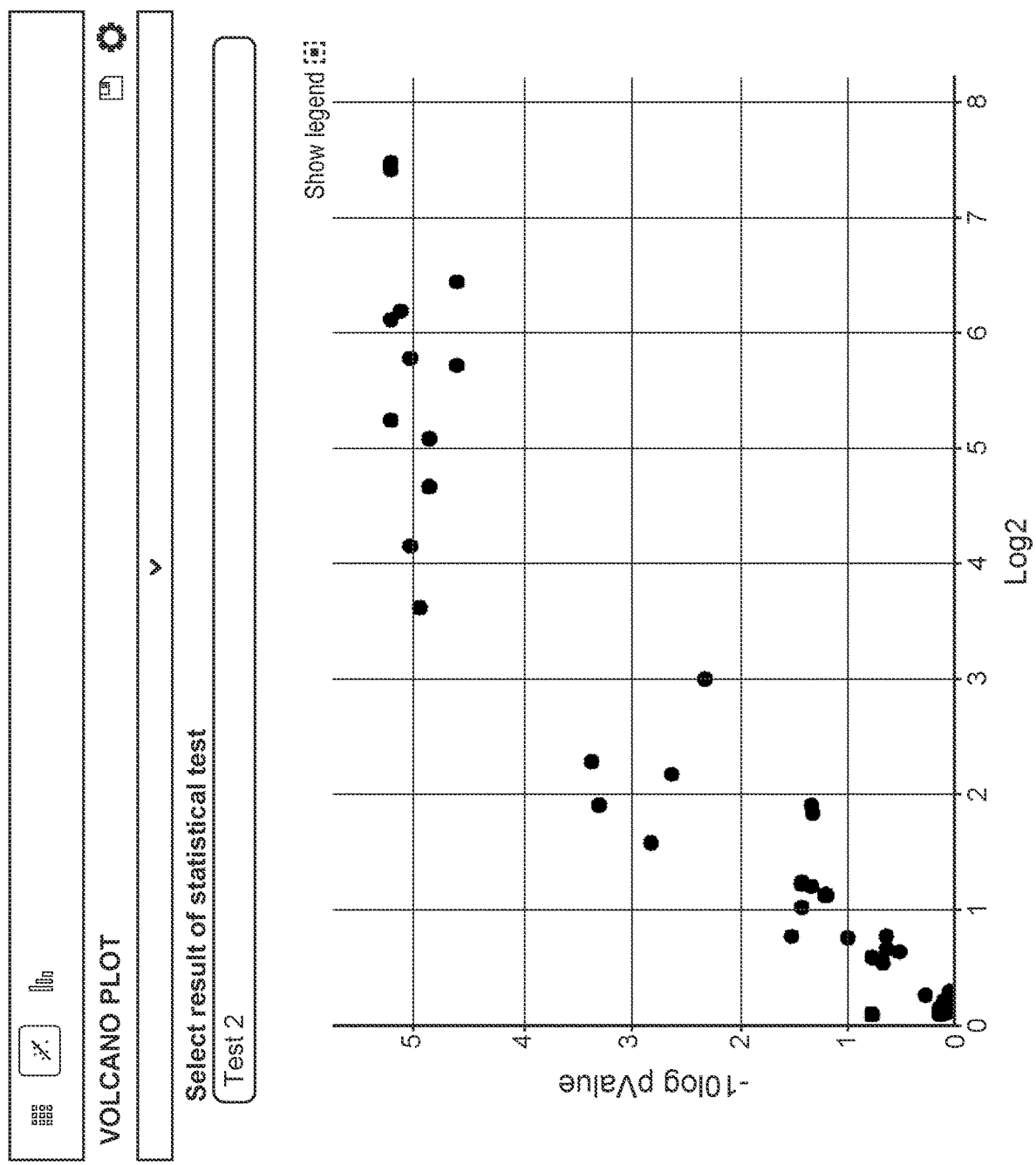

With reference to FIG. 6G, the volcano plot is a scatter plot of a dataset's ratio data (log 2) on the x-axis and the measure of significance (−log 10 of p-values) on the y-axis. This visualization is available for datasets which contain t-tests (p-values). In some embodiments, the volcano plot can be configured to combine individual ratios (e.g., tumor1/stromaAV, tumor2/stromaAV, etc.) into one value using mean. In some embodiments, the volcano plot can be configured show, based on user input, a ratio (e.g., Tumor/Immune or Immune/Tumor) to use in the plot. For example, the volcano plot can be configured show View ratio data as Ratio, Fold changes, or Log 2 ratio. In some embodiments, the volcano plot can be specified using p-values/−10 log using the slider. In some embodiments, the volcano plot can be configured to show different groups of probes by a corresponding color.

Figure 6H:
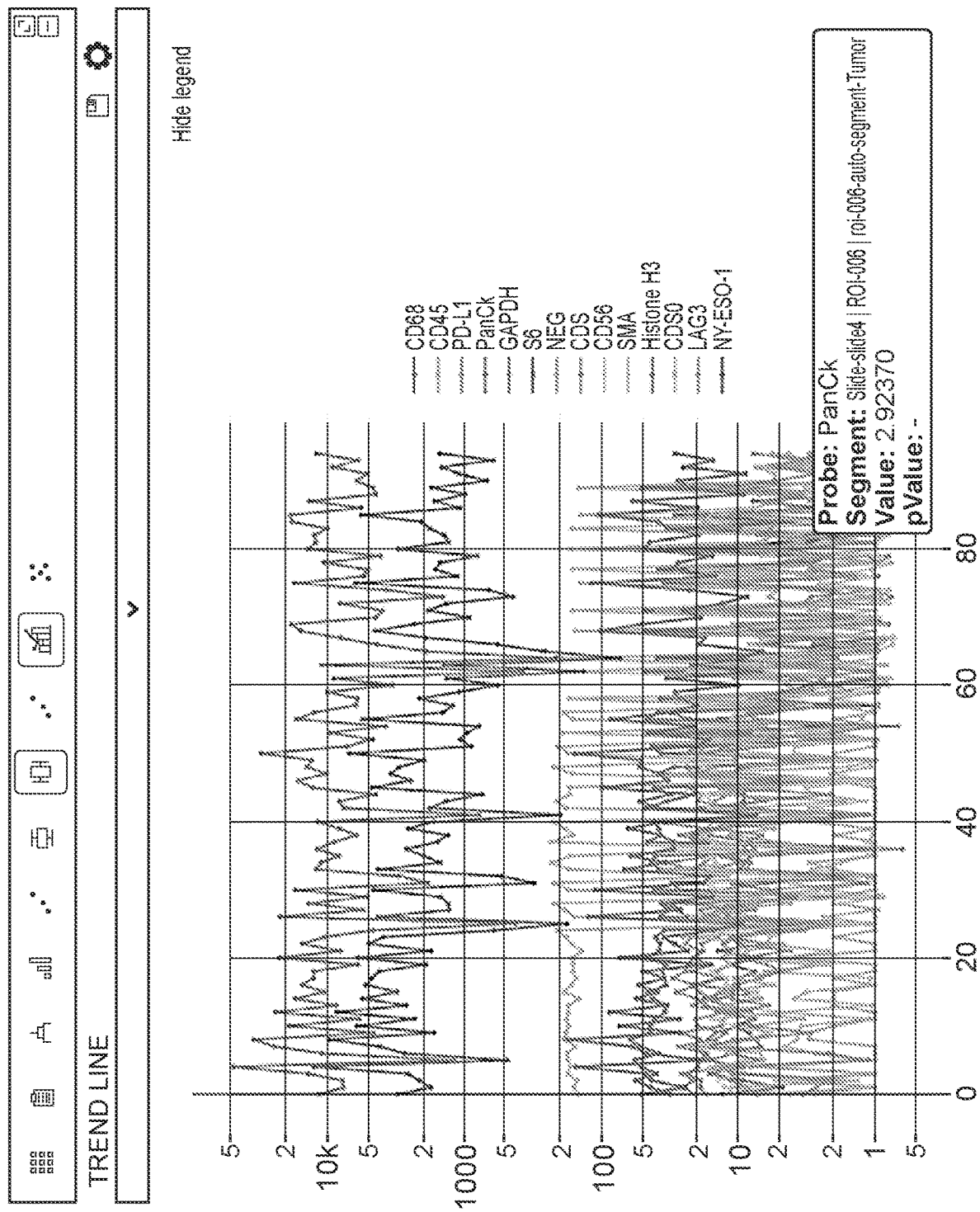
Figure 6I:
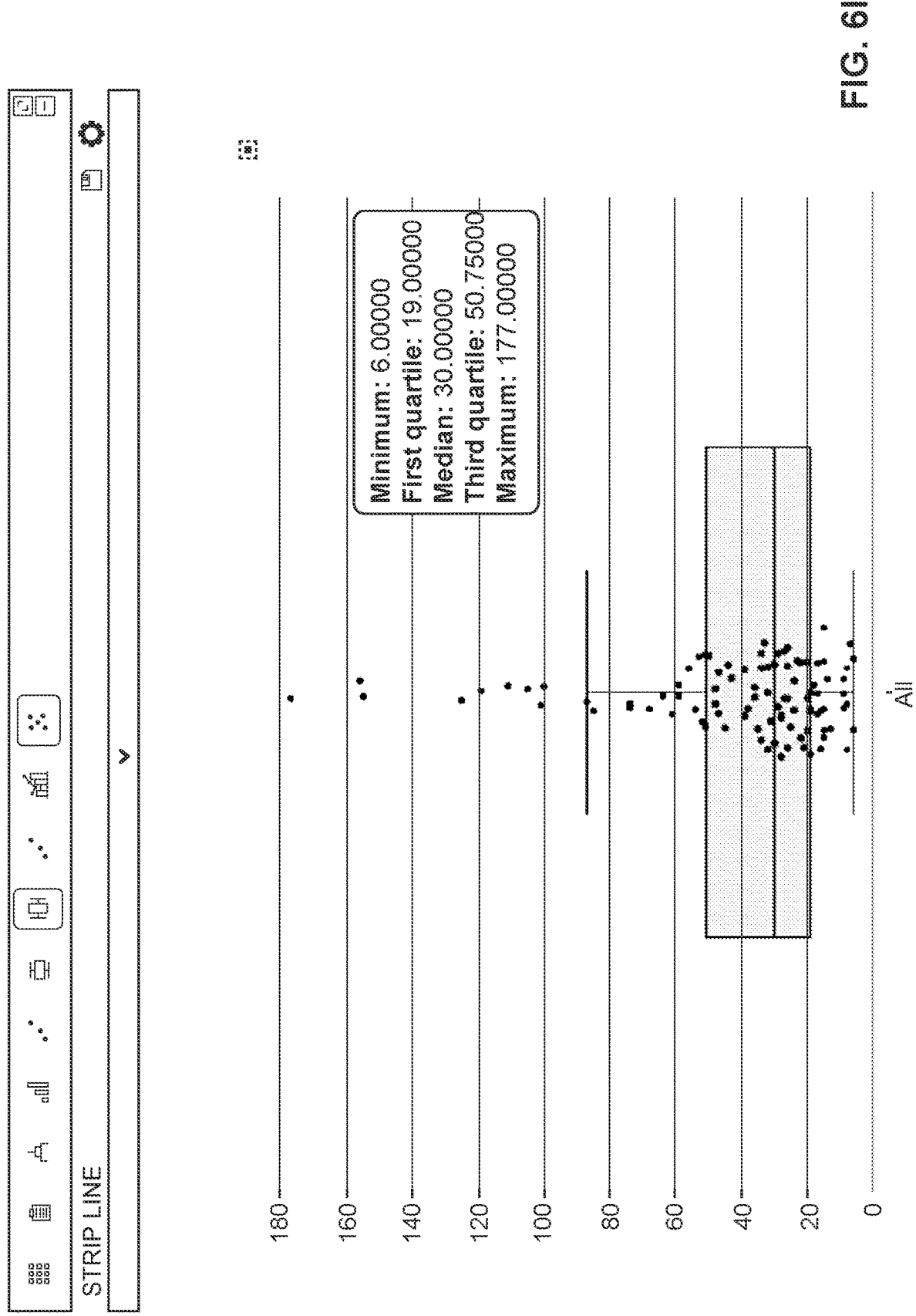
Figure 7A:
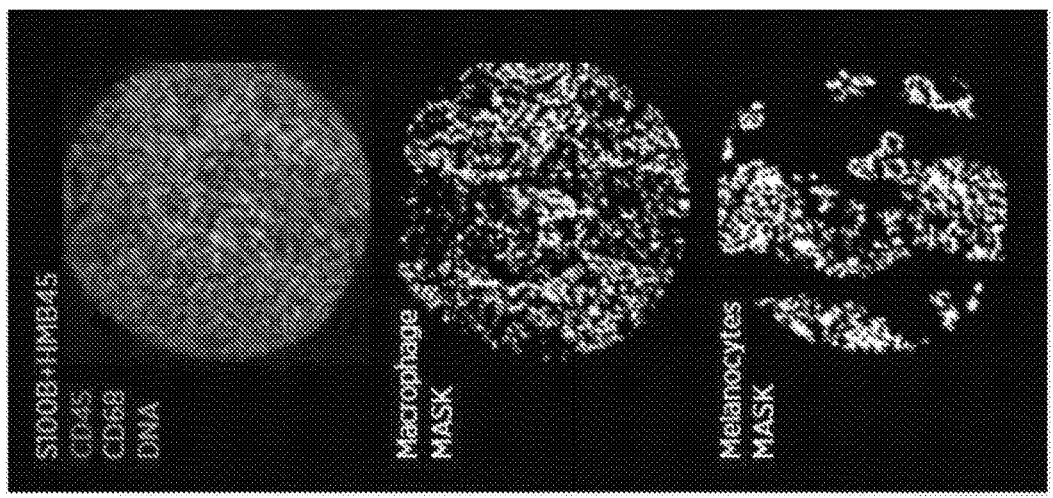
FIGS. 7A-D show exemplary results acquired via the expression mapping system of the present disclosure, in accordance with some embodiments of the present disclosure.
Figure 7B:
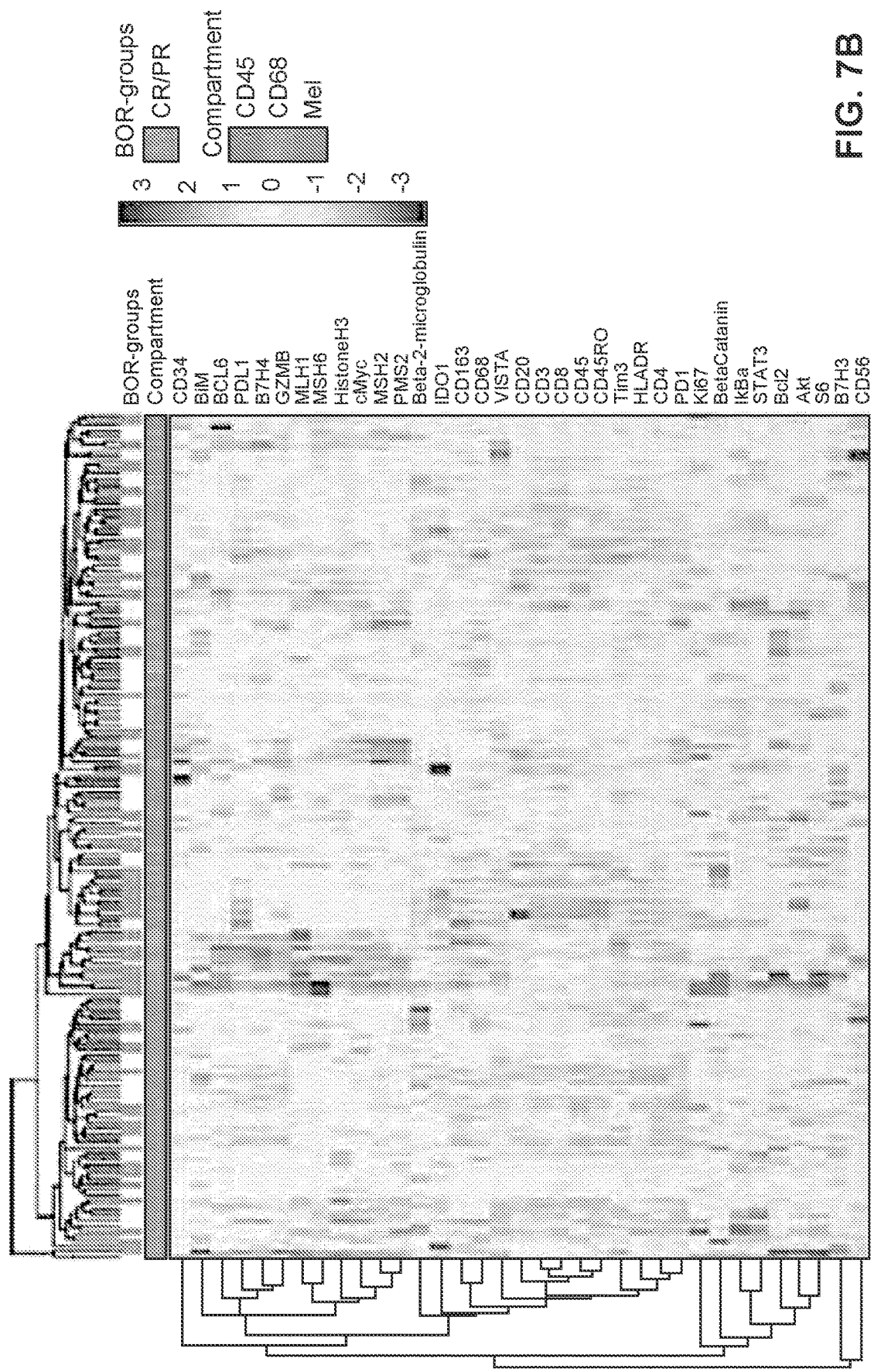
Figure 7C:
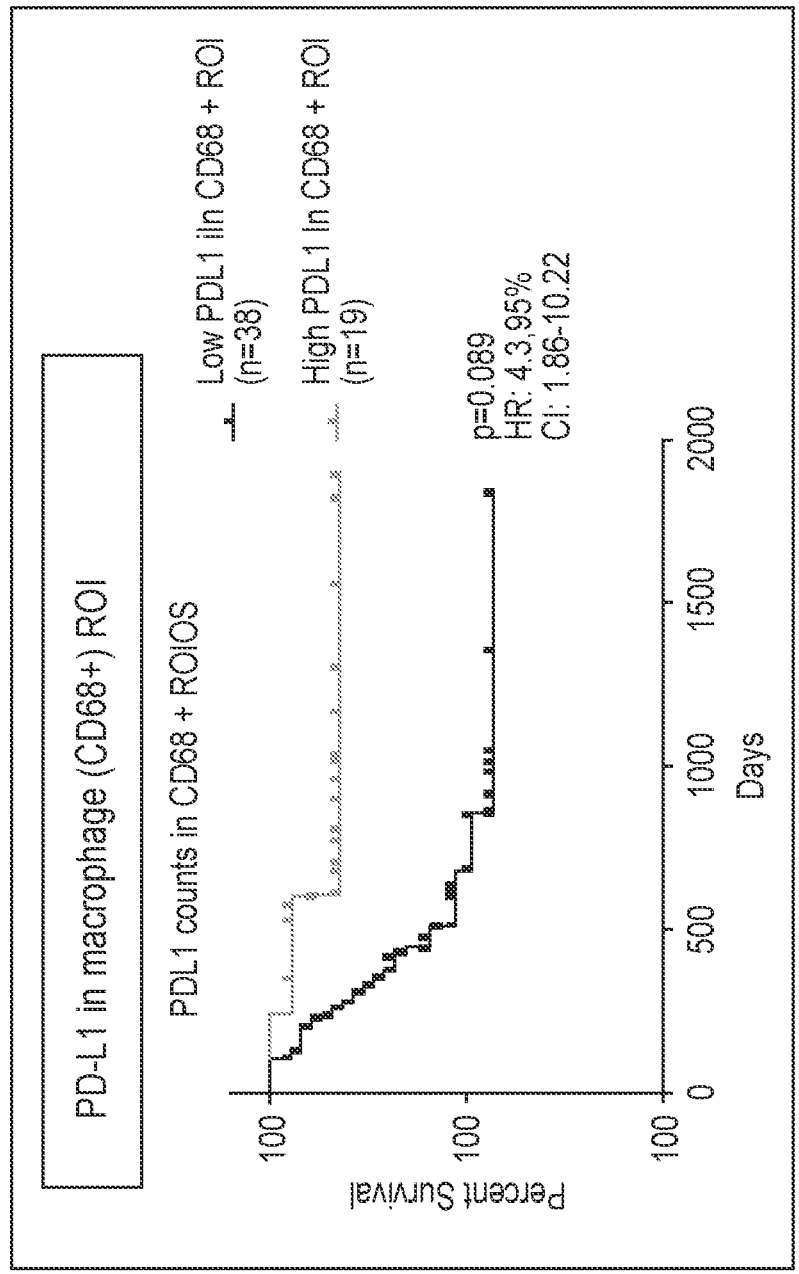
Figure 7D:
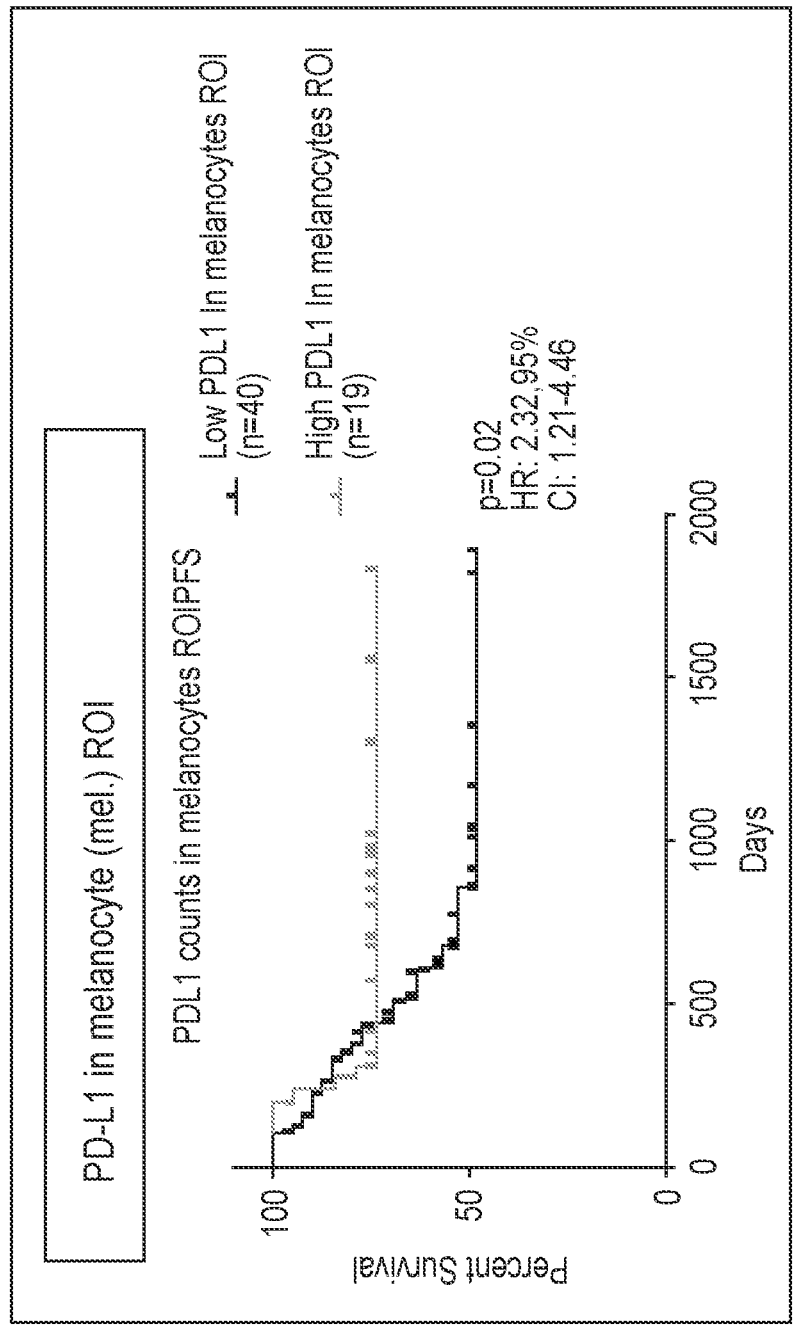

With reference to FIG. 6H, the trend plot shows line graphs for all selected probes in the dataset. Segments can be ordered along the x-axis, while probe counts are along the y-axis. The trend plot can be configured to include various functionality, as follows: hover over lines to see a pop-up with probe names and p-values: switch between linear and log values for the y-axis; choose Segment grouping by tags or factors or to sort segments by tags; select lines on the trend plot via selection of p-value (e.g., maximum p-value) to cause any lines that are representing results associated with that p-value or better to be selected; and drawing a line on the graph using the Select by line button.

With reference to FIG. 6I, the strip plot depicts one probe per visualization. The strip plot can be configured to include various functionality, as follows: dots on the strip plot represent each value; line shows median for group; hover over a data point on the scatter plot to see a popup displaying the target and x- and y-coordinates of the point; hover over any other area on the plot to see the minimum, median, maximum, and quartile values, as well as the probe currently displayed; select p-value that will be used to filter probes for selection (selected p-value or better probes will be shown): view linear counts or Log 2 values; select, based on user input, which probe's plot to view; set p-value: add tags to selected segments create a segment group from selection.

Example 1

FIGS. 7A-D show exemplary results acquired via the expression mapping system of the present disclosure. The spatial mapping embodiments according to the present disclosure helped to identified compartment specific markers associated with potential prognostic biomarkers of survival.

Specific cell types within the tumor microenvironment to identify prognostic biomarkers.

Compartments were elucidated with the Rare Cell Profiling using serial masks, focusing on macrophage (CD68+), melanocyte (S100B+), and non-macrophage immune cells (CD45+CD68−). Aim – to differentiate between the tumor and the stromal areas.

Results: CD3, CD8, β-2 microglobulin, PD-L1, and HLA-DR all demonstrated cell type-specific predictive power both in overall survival rates and progression free survival; PD-L1 showed strongest association with overall survival in the macrophage compartment (FIGS. 7A-D); and β-2 microglobulin in the immune, non-macrophage compartment was associated with both overall survival and progression free survival.

Example 2

Figure 8A:
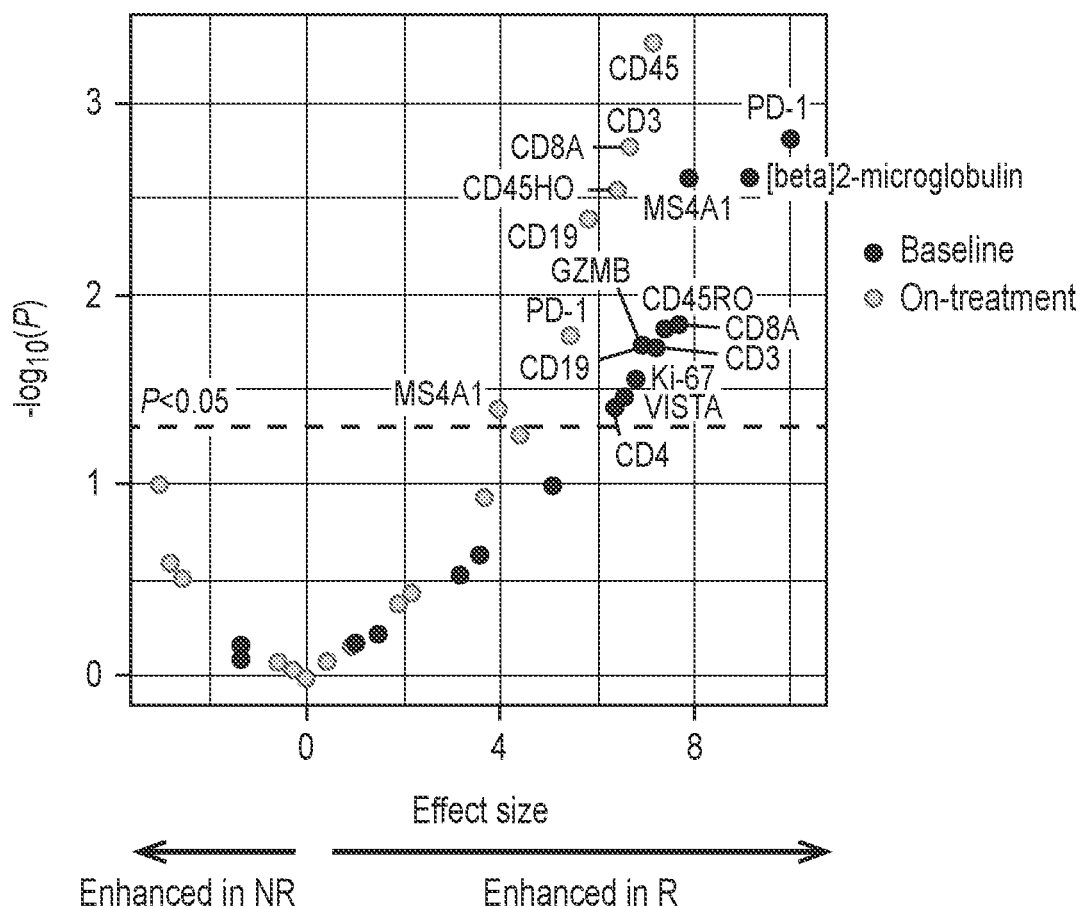
FIGS. 8A-E shows exemplary results acquired via the expression mapping system of the present disclosure, in accordance with some embodiments of the present disclosure.

FIG. 8A shows exemplary results acquired via expression spatial mapping embodiments of the present disclosure. Specifically, FIG. 8A shows biological expression profiling of pretreatment and on treatment biopsy identifies multiple markers associated with response. When tumors were examined from patients during treatment, responders had higher levels of CD45+ expression, CD8+ infiltrate, increased PDL1 PDL1, CD4, granzyme B, FoxP3, CD20 and PD-1 expression over nonresponders. These differences were observed not only in on-treatment samples, but in baseline samples, suggesting that these markers might be used to predict the success of a treatment prior to administration; potentially reshaping the type of therapy selected for the patient.

Example 3

Figure 8B:
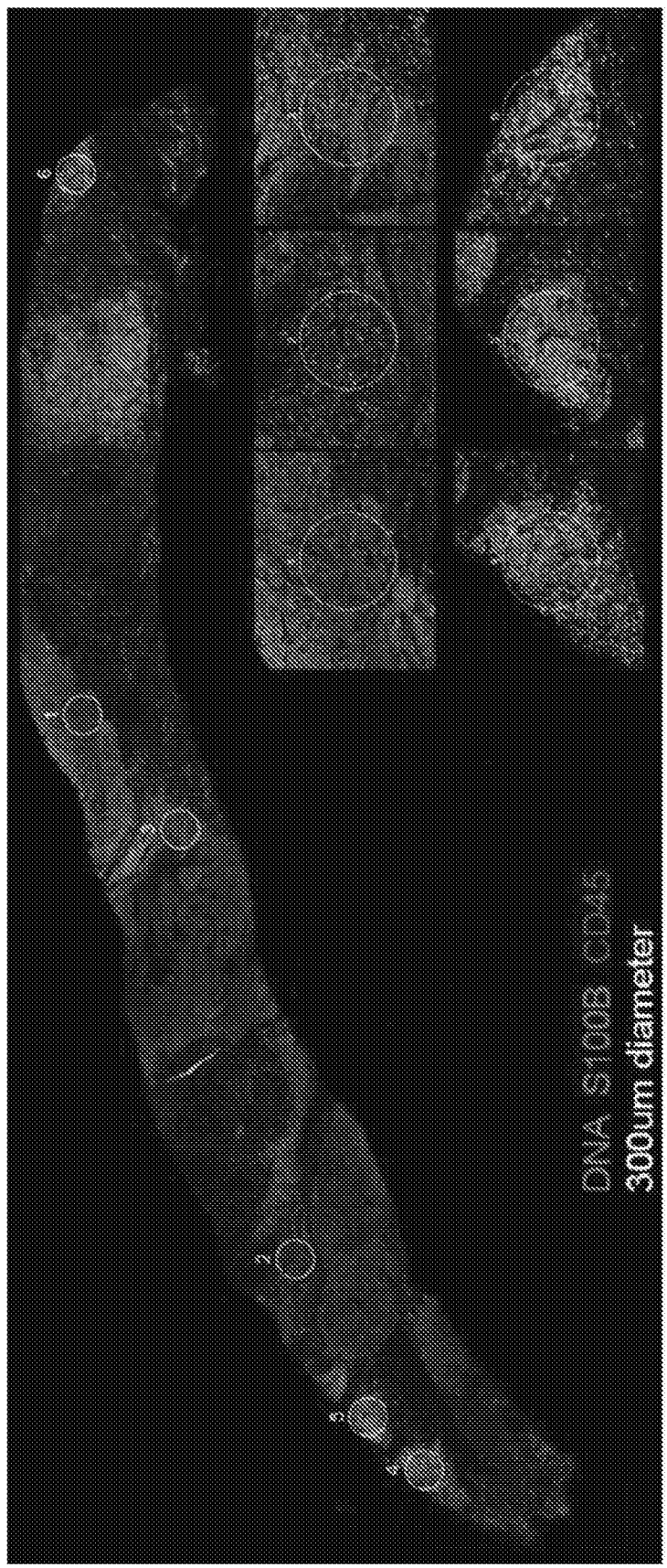
Figure 8C:
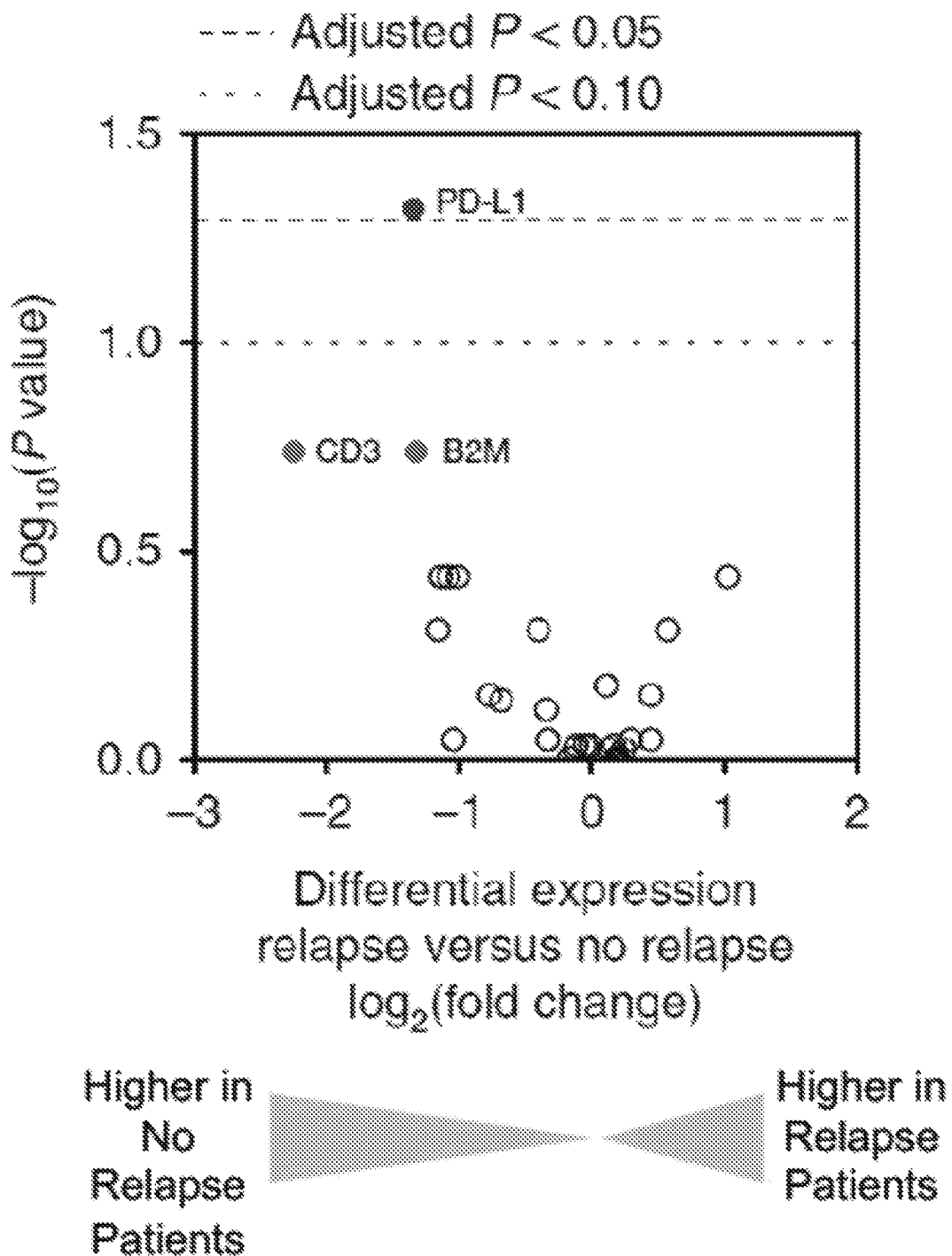

FIGS. 8B-C show exemplary results acquired via the expression spatial mapping embodiments of the present disclosure. In particular, FIG. 8B shows a sample image and ROIs used for a geometric ROI selection strategy, and FIG. 8C shows a volcano plot measuring differential expression of proteins between patients with melanoma that relapsed or did not relapse after neoadjuvant therapy analyzed by GeoMx DSP. Note the increased levels of β2M, CD3, and PD-L1 in patients without relapse. None of the other proteins are shown in the figure and CD3 is associated with the adaptive immune response (figure reproduced from Nature Medicine). See "Neoadjuvant versus Adjuvant Ipilimumab Plus Nivomumab in Macroscopic Stage III Melanoma" (Blank, C U. et al. Neoadjuvant versus Adjuvant Ipilimumab Plus Nivolumab in Macroscopic Stage III Melanoma. Nat Med. 2018; 24(11): 1655-1661), which compared the effects of using I+N as either an adjuvant or a neoadjuvant treatment5.

FFPE biopsies taken prior to treatment with I+N were stained with 29 targets of interest, and S100B an antigen expressed on melanocytes, to identify tumor rich ROI. Six ROIs per tumor were chosen via Geometric Profiling. CD45 staining was also used to establish three ROIs with high immune infiltrate and three ROIs with low immune infiltrate. Levels of CD3, β-2 microglobulin, and PD-L1 protein were quantified with GeoMx DSP, and also stratified IFN-γ RNA levels as low, intermediate, and high.

In this study, neoadjuvant treatment was successful in decreasing the tumor size, resulting in less extensive surgical intervention. Embodiments of the present disclosure aided in finding:

neoadjuvant I+N expands more resident T cell clones than adjuvant I+N as demonstrated by TCR sequencing before and after treatment; and levels of interferon-γ (IFN-γ) RNA within pretreatment tumor biopsies correlated to clinical outcome and relapse rates after treatment.

Patients with decreased levels of CD3, β-2 microglobulin, and PD-L1 and low levels of IFN-γ RNA relapsed. Patients with intermediate to high levels of IFN-γ RNA did not relapse (at time of publication), indicating that this biosignature has the potential to be used to predict the patient's response to treatment (FIG. 5).

Example 4

Figure 8D:
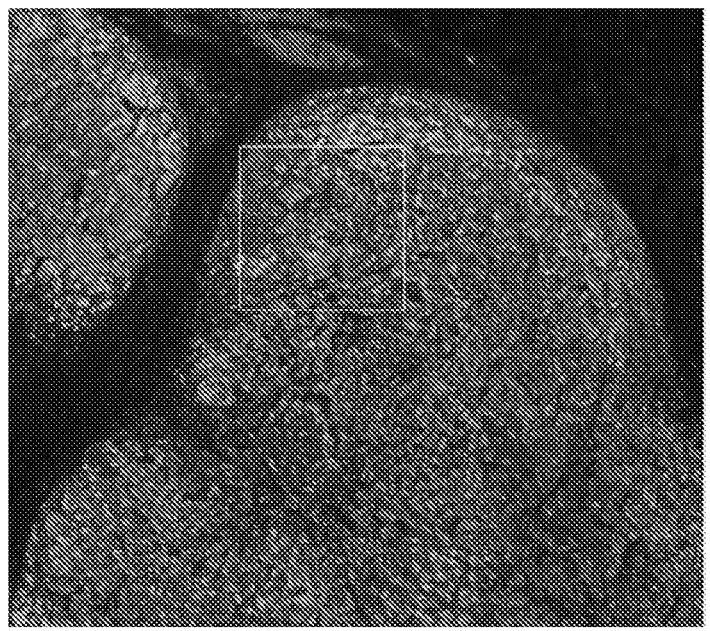
Figure 8E:
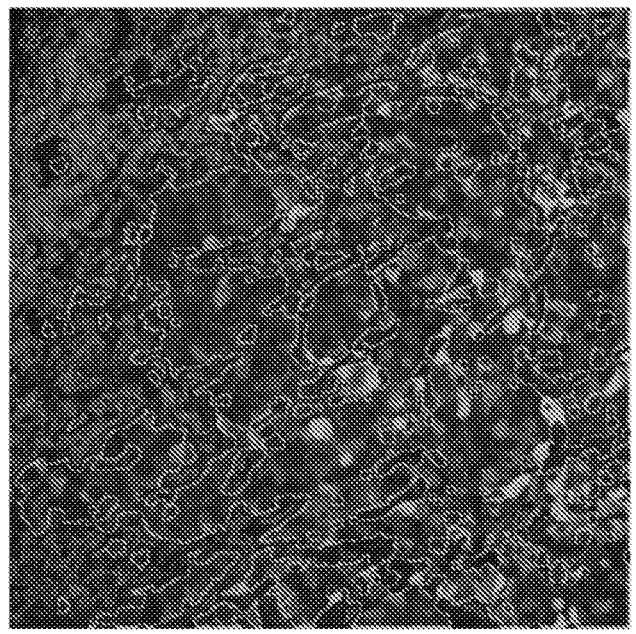

FIGS. 8D-E shows exemplary results acquired via the expression mapping system of the present disclosure. In particular, FIG. 8D shows Tumor sample stained with S100B (tumor cells) and CD45 (immune cells). Segments are generated based on S100B and CD45 cellular morphology; and FIG. 8E shows Enlarged view of segmentation (color coded): Green=S100B-positive tumor cells, red=CD45-positive immune cells, and blue=DNA. Each segment is collected and quantified separately within the ROI.

Figure 9:
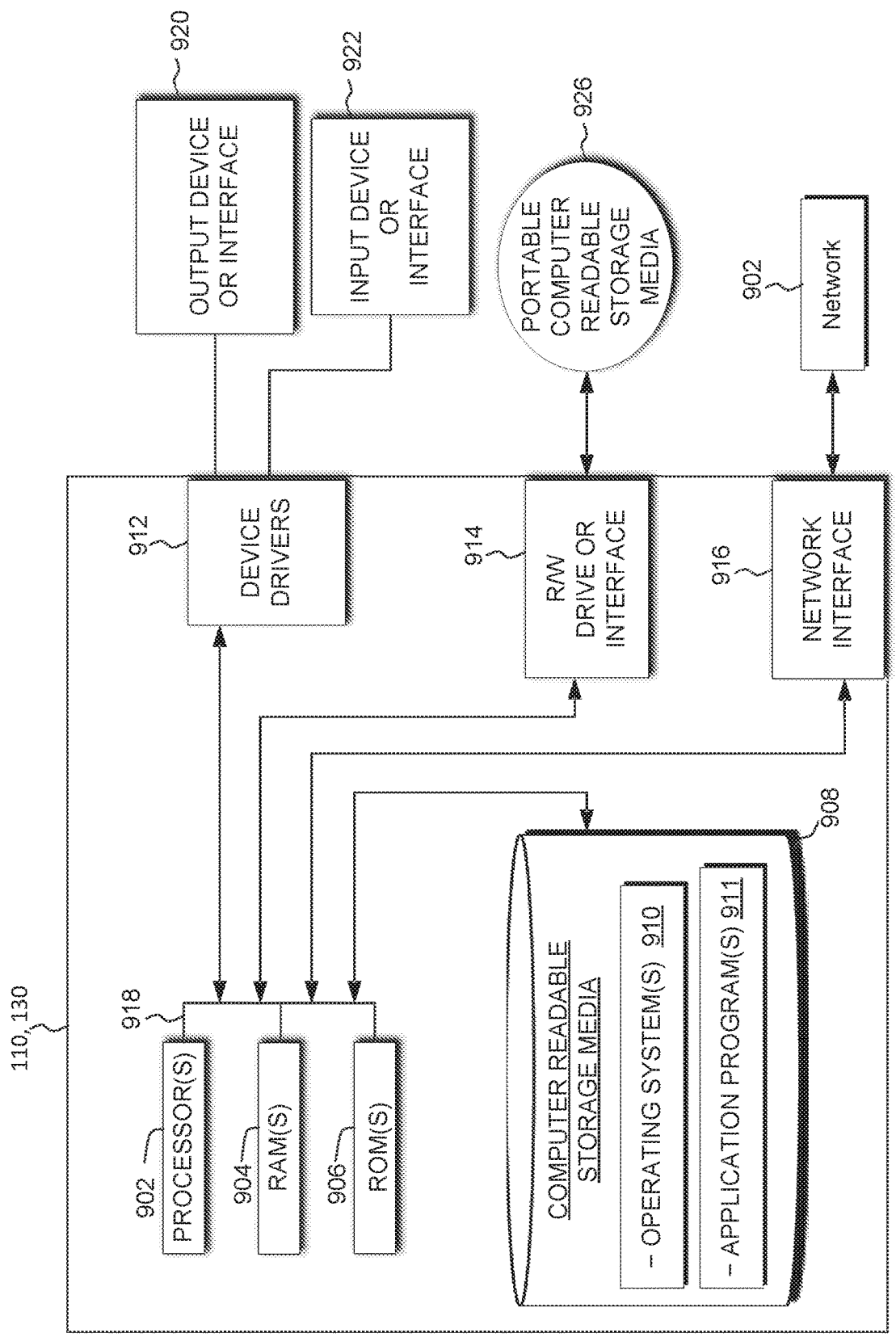
FIG. 9 is a block diagram depicting a user device and/or an expression mapping system, in accordance with some embodiments of the present disclosure.

FIG. 9 is a block diagram depicting user device 110 and/or expression mapping system 130, in accordance with some embodiments of the present disclosure. As shown, user device 110 and/or expression mapping system 130 may include one or more processors 902 (e.g., microprocessors, CPUs, GPUs, etc.), one or more computer-readable RAMs 904, one or more computer-readable ROMs 906, one or more computer readable storage media 908, device drivers 912, read/write drive or interface 914, network adapter or interface 916, all interconnected over a communications fabric 918. The network adapter 916 communicates with a network 930. Communications fabric 918 may be implemented with any architecture designed for passing data and/or control information between processors (such as microprocessors, communications and network processors, etc.), system memory, peripheral devices, and any other hardware components within a system.

One or more operating systems 910 and one or more application programs 911, such as secure mapping application 132, residing on expression mapping platform 130, are stored on one or more of the computer readable storage media 908 for execution by one or more of the processors 902 via one or more of the respective RAMs 904 (which typically include cache memory). In some embodiments, each of the computer readable storage media 908 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable medium (e.g., a tangible storage device) that can store a computer program and digital information.

User device 110 and/or expression mapping system 130 may also include a read/write (R/W) drive or interface 914 to read from and write to one or more portable computer readable storage media 926. Application programs 911 on viewing device 110 and/or user device 120 may be stored on one or more of the portable computer readable storage media 926, read via the respective R/W drive or interface 914 and loaded into the respective computer readable storage media 908. User device 110 and/or expression mapping system 130 may also include a network adapter or interface 916, such as a Transmission Control Protocol (TCP)/Internet Protocol (IP) adapter card or wireless communication adapter (such as a 4G wireless communication adapter using Orthogonal Frequency Division Multiple Access (OFDMA) technology). For example, application programs 911 may be downloaded to the computing device from an external computer or external storage device via a network (for example, the Internet, a local area network or other wide area network or wireless network) and network adapter or interface 916. From the network adapter or interface 916, the programs may be loaded onto computer readable storage media 908. The network may include copper wires, optical fibers, wireless transmission, routers, firewalls, switches, gateway computers and/or edge servers. User device 110 and/or expression mapping system 130 may also include one or more output devices or interfaces 920 (e.g., a display screen), and one or more input devices or interfaces 922 (e.g., keyboard, keypad, mouse or pointing device, touchpad). For example, device drivers 912 may interface to output devices or interfaces 920 for imaging, to input devices or interfaces 922 for user input or user selection (e.g., via pressure or capacitive sensing), and so on. The device drivers 912, R/W drive or interface 914 and network adapter or interface 916 may include hardware and software (stored on computer readable storage media 908 and/or ROM 906).

Expression mapping system 130 can be a standalone network server or represent functionality integrated into one or more network systems. User device 110 and/or expression mapping system 130 can be a laptop computer, desktop computer, specialized computer server, or any other computer system known in the art. In some embodiments, expression mapping system 130 represents computer systems using clustered computers and components to act as a single pool of seamless resources when accessed through a network, such as a LAN, WAN, or a combination of the two. This embodiment may be desired, particularly for data centers and for cloud computing applications. In general, user device 110 and/or expression mapping system 130 can be any programmable electronic device or can be any combination of such devices, in accordance with embodiments of the present disclosure.

The programs described herein are identified based upon the application for which they are implemented in a specific embodiment or embodiment of the present disclosure. That said, any particular program nomenclature herein is used merely for convenience, and thus the embodiments and embodiments of the present disclosure should not be limited to use solely in any specific application identified and/or implied by such nomenclature.

Embodiments of the present disclosure may be or use one or more of a device, system, method, and/or computer readable medium at any possible technical detail level of integration. The computer readable medium may include a computer readable storage medium (or media) having computer readable program instructions thereon for causing a processor to carry out one or more aspects of the present disclosure.

The computer readable (storage) medium can be a tangible device that can retain and store instructions for use by an instruction execution device. The computer readable medium may be, but is not limited to, for example, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire, in accordance with embodiments of the present disclosure.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk. C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform various aspects of the present disclosure.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine or system, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks, in accordance with embodiments of the present disclosure.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams as shown in the Drawings illustrate the architecture, functionality, and operation of possible embodiments of systems, methods, and computer readable media according to various embodiments of the present disclosure. In this regard, each block in the flowchart or block diagrams may represent a module, segment, or portion of instructions, which includes one or more executable instructions for implementing the specified logical function(s). In some embodiments, the functions noted in the blocks may occur out of the order noted in the Drawings. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be understood that although this disclosure includes a detailed description on cloud computing, embodiment of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics can include: on-demand self-service: a cloud consumer can unilaterally provision computing capabilities, such as server time and network storage, as needed automatically without requiring human interaction with the service's provider; broad network access: capabilities are available over a network and accessed through standard mechanisms that promote use by heterogeneous thin or thick client platforms (e.g., mobile phones, laptops, and PDAs); resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter); rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time; measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows: software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings. Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows: private cloud: the cloud infrastructure is operated solely for an organization. It may be managed by the organization or a third party and may exist on-premises or off-premises. Community cloud: the cloud infrastructure is shared by several organizations and supports a specific community that has shared concerns (e.g., mission, security requirements, policy, and compliance considerations). It may be managed by the organizations or a third party and may exist on-premises or off-premises. Public cloud: the cloud infrastructure is made available to the general public or a large industry group and is owned by an organization selling cloud services. Hybrid cloud: the cloud infrastructure is a composition of two or more clouds (private, community, or public) that remain unique entities but are bound together by standardized or proprietary technology that enables data and application portability (e.g., cloud bursting for load-balancing between clouds). A cloud computing environment is service oriented with a focus on statelessness, low coupling, modularity, and semantic interoperability. At the heart of cloud computing is an infrastructure that includes a network of interconnected nodes.

Figure 10:
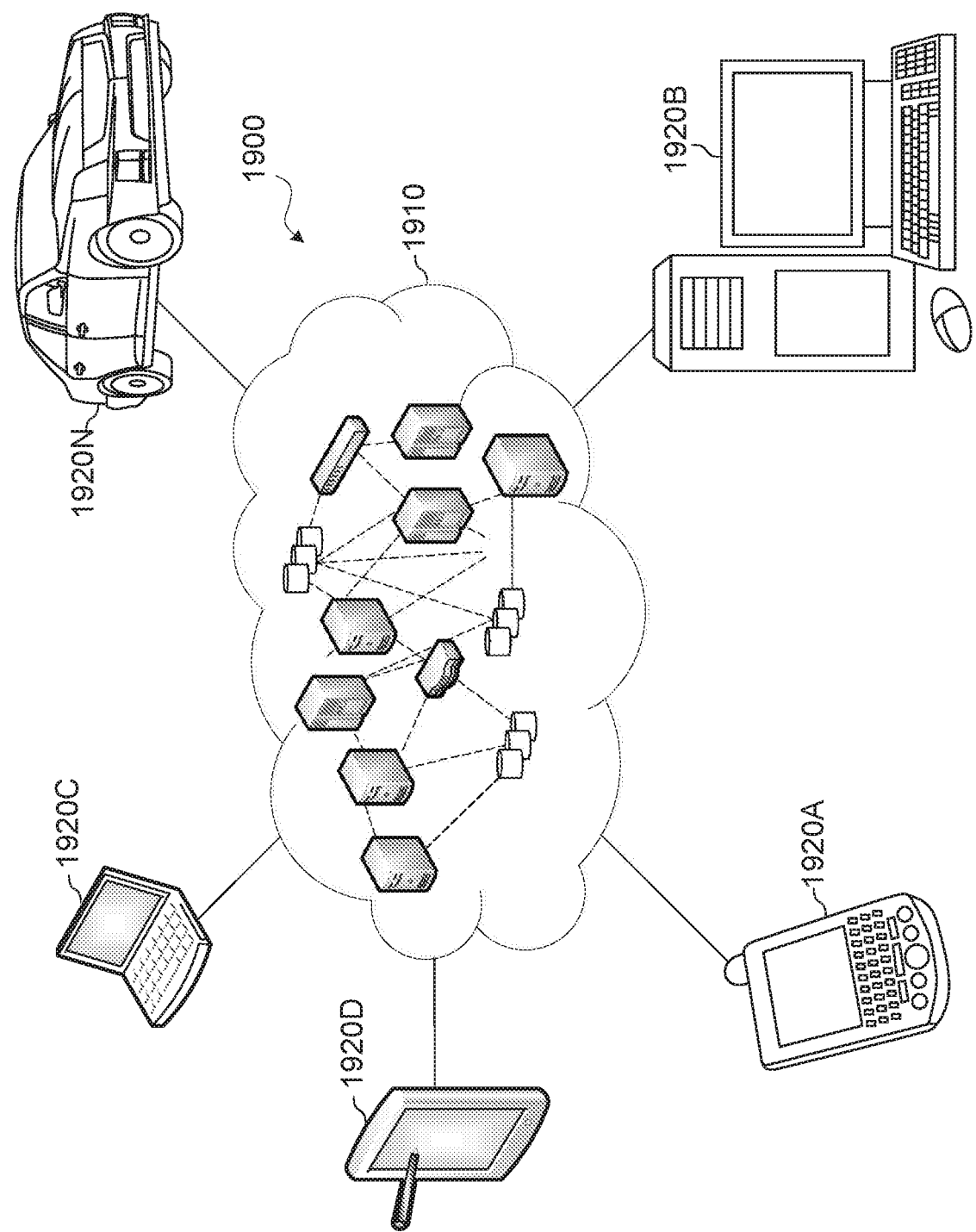
FIG. 10 depicts a cloud computing environment of an expression mapping platform, in accordance with some embodiments of the present disclosure.

Referring now to FIG. 10, illustrative cloud computing environment 1900 is depicted. As shown, cloud computing environment 1900 includes one or more cloud computing nodes (not depicted) with which local computing devices used by cloud consumers, such as, for example, personal digital assistant (PDA) or cellular telephone 1920A, desktop computer 1920B, laptop computer 1920C, and/or automobile computer system 1920N may communicate. The one or more cloud computing nodes may communicate with one another. They may be grouped (not shown) physically or virtually, in one or more networks, such as Private, Community, Public, or Hybrid clouds as described hereinabove, or a combination thereof. This allows cloud computing environment 1900 may be implemented to offer infrastructure, platforms, and/or software as services for which a cloud consumer does not need to maintain resources on a local computing device. The types of computing devices 1920A-N, as shown in FIG. 10, are intended to be illustrative only and that the one or more computing nodes and cloud computing environment 1900 can communicate with any type of computerized device over any type of network and/or network addressable connection (e.g., using a web browser).

Figure 11:
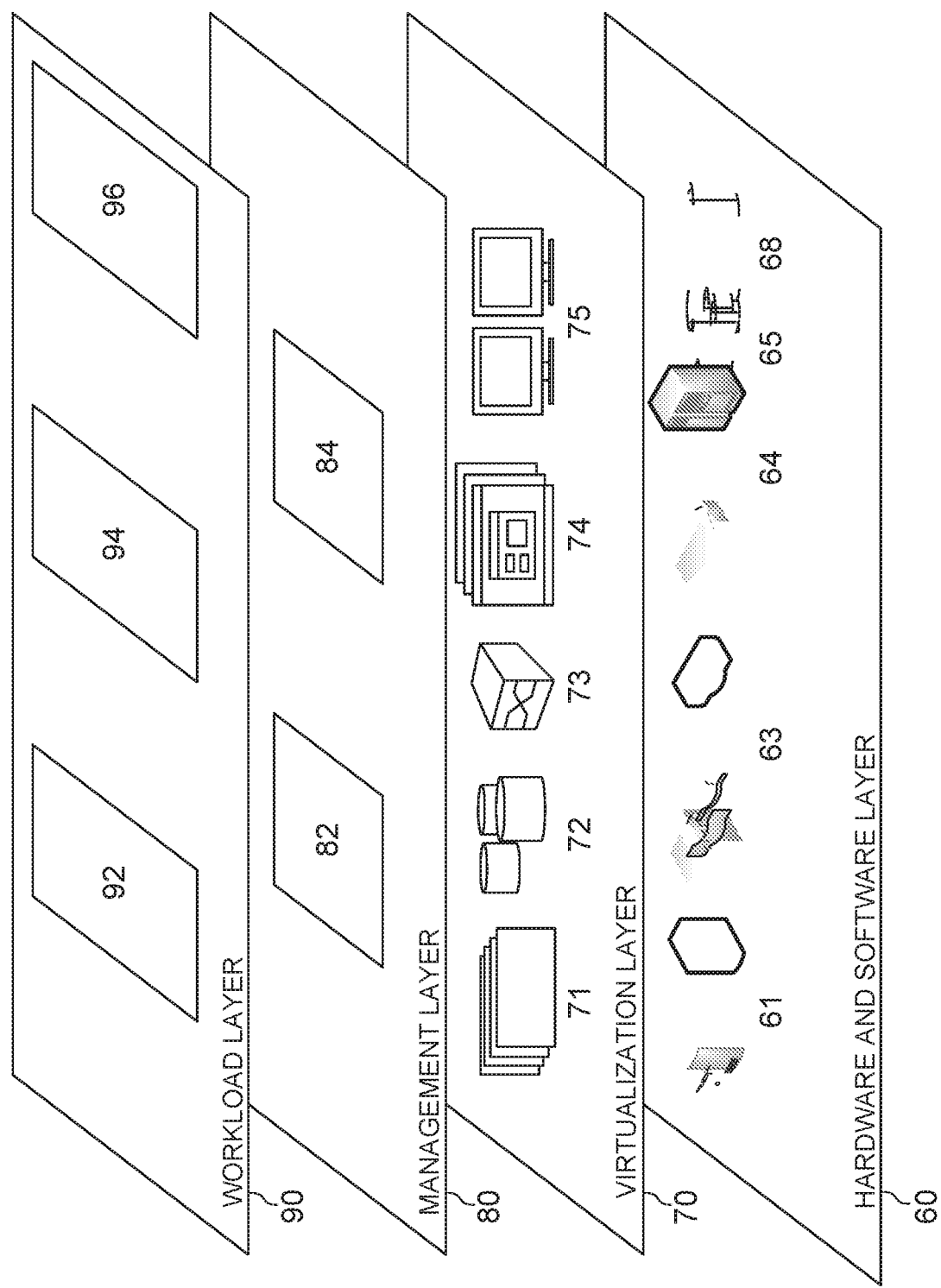
FIG. 11 depicts abstraction model layers of an expression mapping platform, in accordance with some embodiments of the present disclosure.

Referring now to FIG. 11, a set of functional abstraction layers provided by cloud computing environment 1900 is shown. The components, layers, and functions are intended to be illustrative only, and embodiments of the present disclosure are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68. Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

As an example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. For example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which a cloud computing environment (e.g., cloud computing environment 1900) may be utilized. Examples of workloads and functions which may be provided from this layer include: mapping and navigation 91; software development and lifecycle management 92; virtual classroom education delivery 93; data analytics processing 94; transaction processing 95; and expression mapping management 96. Expression mapping management 96 may include functionality enabling the cloud computing environment to be used to perform expression mapping, in accordance with embodiments of the present disclosure.

While various inventive embodiments have been described and illustrated herein, those having ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all structure, parameters, dimensions, materials, functionality, and configurations described herein are meant to be an example and that the actual structure, parameters, dimensions, materials, functionality, and configurations will depend upon the specific application or applications for which the inventive teachings is/are used.

Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the claims supported by the present disclosure, and equivalents thereto, inventive embodiments may be practiced otherwise than as specifically described and claimed. Inventive embodiments of the present disclosure are also directed to each individual feature, system, article, structure, material, kit, functionality, step, and method described herein. In addition, any combination of two or more such features, systems, articles, structure, materials, kits, functionalities, steps, and methods, if such are not mutually inconsistent, is included within the inventive scope of the present disclosure. Some embodiments may be distinguishable from the prior art for specifically lacking one or more features/elements/functionality (i.e., claims directed to such embodiments may include negative limitations).

Also, as noted, various inventive concepts are embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one. B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying." "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures. Section 2111.03.

The terminology used herein was chosen to best explain the principles of the one or more embodiments, practical applications, or technical improvements over current technologies, or to enable understanding of the embodiments disclosed herein. As described, details of well-known features and techniques may be omitted to avoid unnecessarily obscuring the embodiments of the present disclosure.

References in the specification to "one embodiment," "an embodiment," "an example embodiment," or the like, indicate that the embodiment described may include one or more particular features, structures, or characteristics, but it shall be understood that such particular features, structures, or characteristics may or may not be common to each and every disclosed embodiment of the present disclosure herein. Moreover, such phrases do not necessarily refer to any one particular embodiment per se. As such, when one or more particular features, structures, or characteristics is described in connection with an embodiment, it is submitted that it is within the knowledge of those skilled in the art to affect such one or more features, structures, or characteristics in connection with other embodiments, where applicable, whether or not explicitly described.

What is currently claimed:

1. A tissue sample biological expression mapping system configured to spatially map one or more biological expressions of respective target biological components contained in a tissue sample to an image of the tissue sample, the system comprising at least one processor having instructions operational thereon that, when executed, are configured to cause the system to:
   display, in a first display, a scans pane which includes at least an image of the tissue sample positioned on a slide, the image including one or more demarcations each corresponding to a particular one of one or more regions-of-interest (ROIs) selected by a user, each of the selected one or more ROIs corresponding to a specific portion of the tissue sample within the tissue image;
   display, in a second display, a visualization pane comprising a visualization of one or more biological expressions corresponding to the respective target biological components contained within one or more of the selected ROIs, wherein the one or more biological expressions are determined by analyzing cleaved, associated oligonucleotides from each of the selected ROIs; and
   augment the first display by coding the one or more ROIs in the tissue image to show the spatial mapping of the biological expressions within the one or more ROIs.

2. The system of claim 1, wherein coding the one or more ROIs in the tissue image comprises at least color-coding.

3. The system of claim 2, wherein color-coding the one or more ROIs includes presenting a quantitative measurement of the one or more biological expressions.

4. The system of claim 1, wherein the visualization comprises at least one of a graph, a plot, a diagram, and a map of the one or more biological expressions contained in the one or more ROIs.

5. The system of claim 1, wherein the first display is augmented based upon user input specifying at least one selection of a biological expression contained in the visualization.

6. The system of claim 5, wherein the spatial mapping of the at least one user selected biological expression is configured to provide spatial context thereof to at least one of the one or more of the ROIs.

7. The system of claim 1, wherein augmenting the first display is configured to facilitate morphological profiling of tissue in at least one of the one or more ROIs.

8. The system of claim 7, wherein morphological profiling comprises at least one of geometric profiling, segment profiling, contour profiling, gridded profiling, and cell profiling.

9. The system of claim 8, wherein segment profiling comprises at least one of manual segment profiling and automatic segment profiling, the automatic segment profiling configured to automate and facilitate segment profiling of tissue in at least one of the one or more ROIs based on user input specifying at least one segment profiling parameter.

10. The system of claim 8, wherein cell profiling comprises single cell profiling and rare cell profiling.

11. The system of claim 1, wherein:
the one or more biological expressions are determined based upon exposing the tissue sample to a plurality of reagents,
the plurality of reagents include a plurality of imaging reagents configured to bind to biological boundaries of the tissue sample within at least the one or more ROIs, and
each of the plurality of profiling reagents being configured to bind to a specific biological expression of a specific target biological component contained within at least the one or more ROIs.

12. The system of claim 11, wherein each profiling reagent comprises:
a nucleic acid probe including a target binding region in which the cleavable, associated oligonucleotide is removably linked; or
an oligonucleotide including a removably linked antibody.

13. The system of claim 1,
wherein the instructions are configured to cause the system to acquire the image of the tissue sample after the tissue sample is exposed to a plurality of reagents comprising the plurality of profiling reagents, wherein the selected ROIs are selected with respect to shape or size, and wherein the instructions are further configured to cause the system to:
collect the cleaved, associated oligonucleotides; and
analyze the collected, cleaved, associated oligonucleotides to determine the one or more biological expressions contained within one or more of an irradiated ROIs, and their corresponding location therein.

14. The system of claim 1, wherein the instructions are further configured to cause the system to:
display, in a third display, a datasets pane which includes at least one user-selectable dataset, the at least one dataset associated with at least one of the one or more biological expressions contained in the one or more ROIs.

15. The system of claim 1, wherein the scans pane further includes a plurality of icons each corresponding to a specific segment within at least one of the one or more ROIs or the overall tissue image.

16. The system of claim 1, wherein coding the one or more ROIs includes presenting a quantitative measurement of the one or more biological expressions.

17. The system of claim 16, wherein the quantitative measurement corresponds to at least one of a type and degree of respective biological expressions.

18. A non-transitory processor-readable medium storing code representing instructions, the instructions configured to be executed by a processor of a tissue sample biological expression mapping system, and the biological expression mapping system configured to spatially map one or more biological expressions of respective target biological components contained in a tissue sample to an image of the tissue sample, the instructions, when executed, configured to cause the system to:
display, in a first display, a scans pane which includes at least the image of the tissue sample positioned on a slide, the image including one or more demarcations each corresponding to a particular one of one or more regions-of-interest (ROIs) selected by a user, each of the selected one or more ROIs corresponding to a specific portion of the tissue sample within the tissue image;
display, in a second display, a visualization pane comprising a visualization of the one or more biological expressions corresponding to respective target biological components contained within one or more ROIs, wherein the one or more biological expressions are determined by analyzing cleaved, associated oligonucleotides from each of an irradiated ROIs; and
augment the first display by coding the one or more ROIs in the tissue image to show the spatial mapping of the biological expressions within the one or more ROIs.

19. A tissue sample analysis method, comprising:
displaying, in a first display, a scans pane which includes at least an image of the tissue sample positioned on a slide, the image including one or more demarcations each corresponding to a particular one of one or more regions-of-interest (ROIs) selected by a user, each of the selected one or more ROIs corresponding to a specific portion of the tissue sample within the tissue image;
displaying, in a second display, a visualization pane comprising a visualization of one or more biological expressions corresponding to respective target biological components contained within one or more of the ROIs, wherein the one or more biological expressions are determined by analyzing cleaved, associated oligonucleotides from each of the ROIs; and
augmenting the first display or the second display by coding the one or more ROIs in the tissue image to show the spatial mapping of the biological expressions within the one or more ROIs.

* * * * *